US009227946B2

(12) United States Patent
Faldt et al.

(10) Patent No.: US 9,227,946 B2
(45) Date of Patent: *Jan. 5, 2016

(54) 1-[2-(2,4 DIMETHYLPHENYLSULFANYL)-PHENYL]PIPERAZINE AS A COMPOUND WITH COMBINED SEROTONIN REUPTAKE, 5-HT3 AND 5-HT1A ACTIVITY FOR THE TREATMENT OF COGNITIVE IMPAIRMENT

(71) Applicant: H. Lundbeck A/S, Valby-Coppenhagen (DK)

(72) Inventors: Andre Faldt, Ishoj (DK); Rene Holm, Jyllinge (DK); Heidi Lopez de Diego, Naerum (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/242,337

(22) Filed: Apr. 1, 2014

(65) Prior Publication Data

US 2014/0248355 A1    Sep. 4, 2014

Related U.S. Application Data

(62) Division of application No. 12/301,061, filed as application No. PCT/DK2007/050075 on Jun. 15, 2007, now Pat. No. 8,722,684.

(60) Provisional application No. 60/805,014, filed on Jun. 16, 2006, provisional application No. 60/826,666, filed on Sep. 22, 2006, provisional application No. 60/862,826, filed on Oct. 25, 2006.

(30) Foreign Application Priority Data

Jun. 16, 2006  (DK) .................................. 200600824
Sep. 22, 2006  (DK) .................................. 200601223
Oct. 25, 2006  (DK) .................................. 200601384
Mar. 20, 2007  (DK) .................................. 200700427

(51) Int. Cl.
*A61K 31/495* (2006.01)
*C07D 295/096* (2006.01)
*A61K 9/14* (2006.01)

(52) U.S. Cl.
CPC .............. *C07D 295/096* (2013.01); *A61K 9/14* (2013.01); *A61K 31/495* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,573,460 A | 11/1996 | Toji | |
| 6,048,876 A | 4/2000 | Annoura et al. | |
| 7,144,884 B2 | 12/2006 | Ruhland et al. | |
| 7,148,238 B2 | 12/2006 | Ruhland et al. | |
| 7,732,463 B2 | 6/2010 | Puschl et al. | |
| 8,722,684 B2 | 5/2014 | Bang-Andersen et al. | |
| 8,969,355 B2 | 3/2015 | Bang-Andersen et al. | |
| 2011/0053978 A1 | 3/2011 | Miller et al. | |
| 2014/0248356 A1 | 9/2014 | Bang-Andersen et al. | |
| 2014/0256943 A1 | 9/2014 | Faldt et al. | |
| 2014/0315921 A1 | 10/2014 | Bang-Andersen et al. | |
| 2014/0371453 A1 | 12/2014 | Faldt et al. | |
| 2014/0377363 A1 | 12/2014 | Bang-Andersen et al. | |
| 2015/0005318 A1 | 1/2015 | Bang-Andersen et al. | |

FOREIGN PATENT DOCUMENTS

| | | |
|---|---|---|
| CN | 1561336 A | 1/2005 |
| CN | 1606548 A | 4/2005 |
| EP | 2439201 | 4/2012 |
| ES | 2154605 | 4/2001 |
| WO | WO 96/24353 | 8/1996 |
| WO | WO 99/61027 | 12/1999 |
| WO | WO0141701 | 6/2001 |
| WO | WO0149678 | 7/2001 |
| WO | WO0244158 | 6/2002 |
| WO | WO03029232 | 4/2003 |
| WO | WO03053942 | 7/2003 |
| WO | WO 03/105853 | 12/2003 |
| WO | WO2005094896 | 10/2005 |
| WO | WO2006073292 | 7/2006 |
| WO | WO 2007/144006 | 12/2007 |
| WO | WO 2014/044721 | 3/2014 |

OTHER PUBLICATIONS

Advisory Action in U.S. Appl. No. 12/528,440, dated Feb. 28, 2013, 3 pages.
Examiner's Answer to Appeal Brief in U.S. Appl. No. 12/528,440, dated Feb. 3, 2014, 24 pages.
Final Office Action in U.S. Appl. No. 12/528,440, dated Oct. 9, 2012, 22 pages.
Office Action in U.S. Appl. No. 12/528,440, dated Mar. 16, 2012, 20 pages.
Submission in Opposition to European Patent 2 044 043 to H. Lundbeck A/S by Sandoz AG; Sep. 10, 2014, 18 pages.
Response to opposition in European Patent 2 044 043 to H. Lundbeck A/S by Sandoz AG; Sep. 5, 2014, 18 pages.
"Preparation of vortioxetine free base according to example 3a of the opposed patent," Experimental Data, 2 pages, submitted to EPO on Sep. 10, 2014.
Bang-Andersen et al., "Supporting Information," J Med Chem., 2011, 54:S1-S46.
Caira, "Crystalline Polymorphism of Organic Compounds," Topics Current Chem., 1998, vol. 198:163-208, 1 page (Table of Contents Only).

(Continued)

*Primary Examiner* — Savitha Rao
*Assistant Examiner* — Gregg Polansky
(74) *Attorney, Agent, or Firm* — Fish & Richardson P.C.

(57) ABSTRACT

1-[2-(2,4-dimethylphenylsulphanyl)phenyl]piperazine exhibits potent activity on SERT, $5-HT_3$ and $5-HT_{1A}$ and may as such be useful for the treatment of cognitive impairment, especially in depressed patients.

5 Claims, 22 Drawing Sheets

(56) References Cited

OTHER PUBLICATIONS

Figure 1:
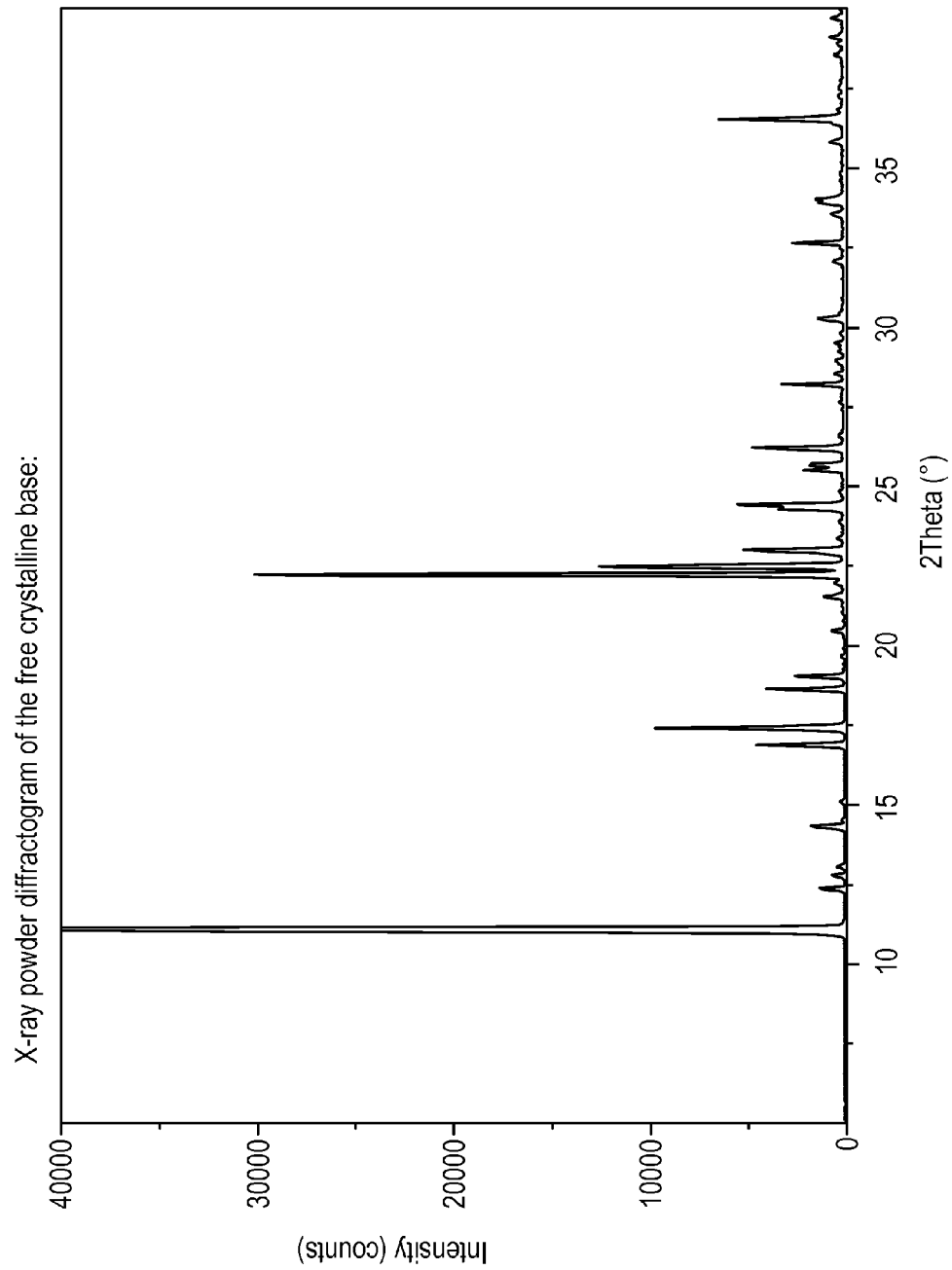

Fava et al., "Effects of Vortioxetine on Cognitive Symptoms of Major Depressive Disorder," 29th CNIP World Congress of Neuropsychopharmacol., Jun. 22-26, 2014, Vancouver, Canada, Poster, 3 pages.

Mahableshwarker et al., "Efficacy of Vortioxetine on Cognitive Function in Adult Patients with Major Depressive Disorder: Results of a Randomized, Double-Blind, Active-Referenced, Placebo-Controlled Trial," 29th CNIP World Congress of Neuropsychopharmacol., Jun. 22-26, 2014, Vancouver, Canada, Poster, 7 pages.

McIntyre et al., "A randomized, double-blind, placebo-controlled study of vortioxetine on cognitive function in depressed adults," Int'l J Neuropsychopharmacol., Online article—published Mar. 20, 2014, 12 pages.

Mutschler et al., "Mutschler Arzneimittelwirkungen," Wissenschatliche Verlagsgesellschaft mbH Stuttgart, 2001, 8:5-15 (with English translation).

Oxman, "Antidepressants and Cognitive Impairment in the Elderly," J Clin Psychiatry, 1996, 57(suppl 5):38-44.

Raskin et al., "Efficacy of Duloxetine on Cognition, Depression, and Pain in Elderly Patients with Major Depressive Disorder: An 8-Week, Double-Blind, Placebo-Controlled Trial," Am J Psychiatry, 2007, 164(6):990-909.

Sanchez et al., "Vortioxetine, a novel antidepressant with multimodal activity: Review of preclinical and clinical data," Pharmacol Therap., Online article—published Jul. 14, 2014, 16 pages.

Waxmonsky, "Assessment and treatment of attention deficit hyperactivity disorder in children with comorbid psychiatric illness," Curr Opin Pediatr., 2003, 15:476-482.

Japanese Office Action mailed Mar. 4, 2014 for JP2012-259835 and its English translation (4 pages).

Response to submissions of the opponent dated Sep. 10, 2014 in EP Patent No. 2 044 043, submission dated Oct. 9, 2014, 3 pages.

Meltzer et al., "Serotonin in aging, late-life depression, and Alzheimer's disease: the emerging role of functional imaging," Neuropsychopharmacology, 1998, 18:407-430.

Nishiyama et al., "Synthesis of N-Arylpiperazines from Aryl Halides and Piperazine under a Palladium Tri-tert-butylphosphine Catalyst", Tetrahedron Letters 39 (1998), pp. 617-620.

Riedel et al., "Specific serotonergic reuptake inhibition impairs vigilance performance acutely and after subchronic treatment," J Psychopharmacol., 2005, 19(1):12-20.

Rushton et al., "Pediatrician and family physician prescription of selective serotonin reuptake inhibitors," Pediatrics, 2000, 105(6):1-6.

Schopfer and Schlapbach, "A general palladium-catalysed synthesis of aromatic and heteroaromatic thioethers" Tetrahedron, Jan. 2001, 57:3069-3073.

Dragheim, "Clinical Study Results for vortioxetine, a novel investigational multimodal antidepressant"; New Therapeutic Opportunities for the Treatment of Depression; 2 pages (2013).

Kaduszkiewicz et al., "Cholinesterase inhibitors for patients with Alzheimer's disease: systematic review of randomised clinical trials"; BMJ; vol. 331; pp. 321-327 (2005).

Katona et al., "A randomized, double-blind, placebo-controlled, duloxetine-referenced, fixed-dose study comparing the efficacy and safety of Lu M21004 in elderly patients with major depressive disorder "; International Clinical Psychopharmacology; vol. 27; pp. 215-223 (2012).

Mork et al., "Vortioxetine (Lu AA21004), a novel multimodal antidepressant, enhances memory in rats"; Pharmacology, Biochemistry and Behavior; vol. 105; pp. 41-50 (2013).

Rogers et al., "A 24-week, double-blind, placebo-controlled trial of donepezil in patients with Alzheimer's disease"; Neurology; http://www.neurology.org/contenI/50/1I136.full.html; vol. 50; pp. 136-145 (1998).

Opposition to European Patent No. 2 044 043 to H. Lundbeck A1S by Sandoz AG; 17 pages (2013).

Prozac Product Insert, Eli Lilly, 2006, 35 pages.

Zoloft Product Insert, Pfizer, 2006, 43 pages.

Lexapro Product Insert. Forest Laboratories. 2003. 28 pages.

Motohashi. N. "Depressive Disorders." in Guidelines for Current Treatments. 2004 edition. pp. 679-680. with English translation (3 pages).

Bang-Andersen et al., Discovery of 1-[2-(2,4-Di methyl phenylsufanl) phenyl] piperazine (Lu AA21 004): A Novel Multimodal Compound for the Treatment of Major Depressive Disorder, J Med Chem 2011, 54:3206-3221.

Cartensen, J.T., "Preformulation," in Banker et al. (ed), Modern Pharmaceutics, Fourth Ed., 2002, pp. 172-174.

Bavin, M., Polymorphism in Process Development, Chemistry and Industry, 1989, 21:527-529.

Berge et al., Pharmaceutical Salts, Journal of Pharmaceutical Sciences, 1977, 66:1-19.

Brent, R., Investigating Differences in Solubility Between Crystalline and Amorphous Forms of Pharmaceuticals, EYP 2006, conference presentation, Session 5, May 14, 2006, Pharm. Res 17:2000.

Byrn et al., Pharmaceutical Solids: A Strategic Approach to Regulatory Considerations, Phannaceutical Research, 1995, 12:945-954.

Hancock et al., Molecular Mobility of Amorphous Pharmaceutical Solids Below Their Glass Transition Temperatures, Pharmaceutical Research, 1995, 12:799-805.

Huang et al., Impact of solid state properties on developability assessment of drug candidates, Advanced Drug Delivery Reviews, 2004, 56:321-334.

Notice of Opposition, filed in counterpart application No. EP 07 764 495.3 (Patent EP 2 044 043 B1), dated Oct. 30, 2012.

Prim et al., Palladium-catalysed reactions of aryl halides with soft, non-organometallic nucleophiles, Tetrahedron, 2002, 58:2041-2075.

ICH Harmonized Tripartite Guideline, Current Step 4 version dated Oct. 6, 1999, Specifications: Test Procedures and Acceptance Criteria for New Drug Substances and New Drug Products: Chemical Substances Q6A, 36 pages.

Winter. G., Polymorphs and Solvates of Molecular Solids, in the Pharmaceutical Industry, Reactivity of Molecular Solids, Boldyreva et al. (eds.), Wiley, 1999, Chapter 7, pp. 241-242.

MedicineNet, "Cancer", http://www.medterms.com, 2 pages, downloaded on Apr. 7, 2008.

Vickers, Drugs and Aging, 2002, vol. 19(7), pp. 487-494.

English translation of Chinese Office Action for CN201210034684.8 dated Dec. 3, 2013 (19 pages).

Ruhland, et al., "Iron-Assisted Nucleophilic Aromatic Substitution on Solid Phase", Mar. 15, 2002, J. Org. Chem. 2002, 67, pp. 5257-5268.

Smith et al., "The synthesis and SAR of 2-arylsulfanyl-phenyl piperazinyl acetic acids as glyT-1 inhibitors", Mar. 8, 2004, Bioorganic Medicinal Chemistry Letters 14 (2004), pp. 4027-4030.

Morita et al., "Practical Application of the Palladium-catalyzed Amination in Phenylpiperazine Synthesis: An Efficient Synthesis of a Metabolite of the Antipsychotic Agent Aripiprazole", Dec. 25, 1997, Tetrahedron vol. 54 (1998), pp. 4811-4818.

Murata et al., "A general and efficient method for the palladium-catalyzed cross-coupling of thiols and secondary phosphines", Mar. 30, 2004, Tetrahedron vol. 60 (2004), pp. 7397-7403.

Anagnostaras et al., "Hippocampus and Contextual Fear Conditioning: Recent Controversies and Advances," Hippocampus, 2001, 11:8-17.

Anagnostaras et al., "Temporally Graded Retrograde Amnesia of Contextual Fear after Hippocampal Damage in Rats: Within-Subjects Examination," J Neurosci., 1999, 19:1106-1114.

Barnes et al., "The effects of ondansetron, a 5-HT3 receptor antagonist, on cognition in rodents and primates," Pharamcol Biochem Behav., 1990, 35:955-962.

Boast et al., "5HT antagonists attenuate MK801-impaired radial arm maze performance in rats," Neurobiol Learn Mem., 1999, 71:259-271.

Carey et al., "Ondansetron and arecoline prevent scopolamine-induced cognitive deficits in the marmoset," Pharamcol Biochem Behav., 1992, 42:75-83.

Chung et al., "Clozapine increases both acetylcholine and dopamine release in rat ventral hippocampus: role of 5-$HT_{1A}$ receptor agonism," Brain Res., 2004, 1023:54-63.

(56) References Cited

OTHER PUBLICATIONS

Costall and Naylor., "5-$HT_3$ Receptors," Current Drug Targets—CNS & Neurobiol Disord., 2004, 3:27-37.
DeBattista et al., "A Placebo-Controlled, Randomized, Double-Blind Study of Adjunctive Bupropion Sustained Release in the Treatment of SSRI-Induced Sexual Dysfunction," J.Clin.Psych., 2005, 66:844-848.
Diez-Ariza et al., "Flumazenil and tacrine increase the effectiveness of ondansetron on scopolamine-induced impairment of spatial learning in rats," Psychopharmacology, 2003, 169:35-41.
Faerber et al., "The neuronal 5-$HT_3$ receptor network after 20 years of research—Evolving concepts in management of pain and inflammation," Eur J Pharmacol., 2007, 560:1-8.
Fairweather et al., "A Double Blind Comparison of the Effects of Fluoxetine and Amitriptyline on Cognitive Function in Elderly Depressed Patients," Hum Psychpharmacol., 1993, 8:41-47.
Fanselow, "Conditioned and unconditional components of postshock freezing," Pavlov J. Biol. Sci, 1980, 15:177-182.
Fava and Rush, "Current Status of Augmentation and Combination Treatments for Major Depressive Disorder: A Literature Review and a Proposal for a Novel Approach to Improve Practice," Psychother. Psychosom., 2006, 75:139-153.
Fenik et al., "Hypoglossal Nerve Response to 5-$HT_3$ Drugs Injected into the XII Nucleus and Vena Cava in the Rat," Sleep, 2001, 8:871-878.
Gil-Bea et al., "Facilitation of cholinergic transmission by combined treatment of ondansetron with flumazenil after cortical cholinergic deafferentation," Neuropharmcol., 2004, 47:225-232.
Giovannini et al., "Serotonergic Modulation of Acetylcholine Release from Cortex of Freely Moving Rats," J Pharmacol Exp Ther., 1998, 285:1219-1225.
Harmer et al., "Acute administration of citalopram facilitates memory consolidation in healthy volunteers," Psycopharmacol., 2002, 163:106-110.
Heilig and Egli, "Pharmacological treatment of alcohol dependence: Target symptoms and target mechanisms," Pharmacol. Therapeut., 2006, 111:855-876.
Koyama et al., "Enhancement of cortical and hippocampal cholinergic neurotransmission through 5-HT1A receptor-mediated pathways by BAY x 3702 in freely moving rats," Neurosci Lett., 1999, 265:33-36.
Levkovitz et al., "The SSRIs drug Fluoxetine, but not the noradrenergic tricyclic drug Desipramine, improves memory performance during acute major depression," Brain Res. Bull, 2002, 58:345-350.
McGurk and Meltzer, "The role of cognition in vocational functioning in schizophrenia," Scizophrenia Res., 2000, 45:175-184.
Meneses and Hong, "5-HT1A Receptors Modulate the Consolidation of Learning in Normal and Cognitively Impaired Rats," Neurobiol Learning Memory, 1999, 71:207-218.
Napiorkowska-Pawlak et al., "Attenuation of the acute amnestic effect of ethanol by ifenprodil: comparison with ondansetron and dizocilpine," Fundam Clin Pharmacol., 2000, 14:125-131.
Nelson et al., "Nonhormonal Therapies for Menopausal Hot Flashes Systematic Review and Meta-analysis," JAMA, 2006, 295:2057-2071.
Paradiso et al., "Cognitive impairment in the euthymic phase of chronic unipolar depression," J. Nervous Mental Disease, 1997, 185:748-754.
Phillips and LeDoux, "Differential contribution of amygdala and hippocampus to cued and contextual fear conditioning," Behav. Neurosci., 1992, 106:274-285.
Preston, "5-$HT_3$ Antagonists and Disorders of Cognition," Recent Advances in the treatment of Neurodegenerative disorders and cognitive function, 1994, (eds.) Racagni and Langer, Basel Karger, p. 89-93.
Radulovacki et al., "Serotonin 5-$HT_3$ -receptor Antagonist GR 38032F Suppresses Sleep Apneas in Rats," Sleep, 1998, 21:131-136.
Ravnkilde et al., "Cognitive deficits in major depression," Scand. J. Psych., 2002, 43:239-251.
Rybakowski et al., "Prefrontal cognition in schizophrenia and bipolar illness in relation to Va166Met polymorphism of the brain-derived neurotrophic factor gene," Psychiatry Clin. Neurosci., 2006, 60:70-76.
Sokolski et al., "Once-daily high-dose pindolol for SSRI-refractory depression," Psych. Res., 2004, 125:81-86.
Sumiyoshi et al., "Enhancement of Cognitive Performance in Schizophrenia by Addition of Tandospirone to Neuroleptic Treatment," Am.J.Psych, 2001, 158:1722-1725.
Tack et al., "Systematic review: the efficacy of treatments for irritable bowel syndrome—a European perspective," Aliment Pharmacol. Ther., 2006, 24:183-205.
Statement of Arguments by the Opponent, Teva Pharmaceutical Industries LTD., Israeli Patent Application 195511, dated Nov. 30, 2014, 21 pages.
Bandelin, "Compressed Tablets by Wet Granulation," in Pharmaceutical Dosage Forms: Tablets, ed. by Lieberman et al., 1989, pp. 131-193.
Bastin et al., "Salt Selection and Optimisation Procedures for Pharmaceutical New Chemical Entities," Organic Proc Res Devel., 2000, 4:427-435.
Bernstein, "Polymorphism in Molecular Crystals," 2002, pp. 8-11.
Gould, "Salt selection for basic drugs," Int'l J Pharm., 1986, 33:201-217.
Hilfiker, "Relevance of Solid state Properties for Pharmaceutical Products," in Polymorphism in the Pharmaceutical Industry, 2006, pp. 1-19.
Mealy and Bayes, "Annual Update 2003-2004: Treatment of Psychiatric Disorders," Drugs of the Future, 2004, 29(9):923-977.
Rubinstein, "Tablets," in Pharmaceutics: the Science of Dosage Form Design, ed. by Aulton, 1988, pp. 304-321.
Decision Rejecting the Opposition in European Application 07 764 495.3 (2 044 043), dated Dec. 19, 2014, 13 pages.
Grounds of Appeal by Sandoz, filed in European Application No. 07 764 495.3 (2 044 043), dated Apr. 29, 2015, 23 pages.
"Attention Deficit Hyperactivity Disorder (ADHD)", National Institutes of Mental Health, NIH publication No. 12-3572, revised 2012, 28 pages, downloaded from "www.nimh.nih.gov/health/publications/attention-deficit-hyperactivitydisorder/index.shtml?rf=71264" on Mar. 30, 2015.
"Cognitive Impairment: A call for Action, Now!" U.S. Centers for Disease Control and Prevention, Feb. 2011, 4 pages, downloaded from "www.cdc.gov/aging/pdf/cognitive_impairmenUcogimp_poilicy_final.pdf" on Mar. 30, 2015.
Pehrson et al., "The Novel Multimodal Antidepressant Vortioxetine, (Lu AA21004) Improves Memory Performance in 5-HT Depleted Rats via 5-HT3 and 5-HT1A Receptor Mechanisms"; Poster Presented at 25th Congress of European College of Neuropsychopharmacology (ECNP), Oct. 13-17, 2012, 1 page.

1-[2-(2,4 DIMETHYLPHENYLSULFANYL)-PHENYL]PIPERAZINE AS A COMPOUND WITH COMBINED SEROTONIN REUPTAKE, 5-HT3 AND 5-HT1A ACTIVITY FOR THE TREATMENT OF COGNITIVE IMPAIRMENT

CROSS REFERENCE TO PRIOR APPLICATIONS

This is a divisional application of U.S. application Ser. No. 12/301,061, filed Nov. 17, 2008, which is a U.S. National Phase application under 35 U.S.C. §371 of International Patent Application No. PCT/DK2007/050075, filed Jun. 15, 2007, and claims the benefit of Danish Patent Application No. PA 2006 00824, filed Jun. 16, 2006; U.S. Provisional Application No. 60/805,014, filed Jun. 16, 2006; Danish Patent Application No. PA 2006 01223, filed Sep. 22, 2006; U.S. Provisional Application No. 60/826,666, filed Sep. 22, 2006; Danish Patent Application No. PA 2006 01384, filed Oct. 25, 2006; U.S. Provisional Application No. 60/862,826, filed Oct. 25, 2006; and Danish Patent Application No. PA 2007 00427, filed Mar. 20, 2007, all of which are incorporated by reference herein. The International Application published in English on Dec. 21, 2007 as WO 2007/144005 under PCT Article 21(2).

FIELD OF THE INVENTION

The present invention relates to compounds, which exhibit serotonin reuptake inhibition activity combined with an activity on the serotonin receptor 1A (5-$HT_{1A}$) and the serotonin receptor 3 (5-$HT_3$), and which as such are useful in treatment of CNS related diseases.

BACKGROUND OF THE INVENTION

Selective serotonin reuptake inhibitors (SSRI) have for years been the first choice therapeutics for the treatment of certain CNS related diseases, in particular depression, anxiety and social phobias because they are effective, well tolerated and have a favourable safety profile as compared to previously used compounds, i.e. the classical tri-cyclic compounds.

Nonetheless, therapeutic treatment using SSRI is hampered by a significant fraction of non-responders, i.e. patients who do not respond or only respond to a limited extent to the SSRI treatment. Moreover, typically an SSRI treatment does not begin to show an effect until after several weeks of treatment.

In order to circumvent some of these shortcomings of SSRI treatment, psychiatrists sometimes make use of augmentation strategies. Augmentation of antidepressants may be achieved e.g. by combination with mood stabilisers, such as lithium carbonate or triiodothyronin, or by the parallel use of electroshock.

It is known that a combination of inhibition of the serotonin transporter (SERT) with an activity on one or more serotonin receptors may be beneficial. It has previously been found that the combination of a serotonin reuptake inhibitor with a compound having 5-$HT_{2C}$ antagonistic or inverse agonistic effect (compounds having a negative efficacy at the 5-$HT_{2C}$ receptor) provides a considerable increase in the level of 5-HT (serotonin) in terminal areas, as measured in microdialysis experiments (WO 01/41701). This would imply a shorter onset of antidepressant effect in the clinic and an augmentation or potentiation of the therapeutic effect of the serotonin reuptake inhibitor (SRI).

Similarly, it has been reported that the combination of pindolol, which is a 5-$HT_{1A}$ partial agonist, with a serotonin reuptake inhibitor gives rise to fast onset of effect [*Psych. Res.*, 125, 81-86, 2004].

CNS related diseases, such as e.g. depression, anxiety and schizophrenia are often co-morbid with other disorders or dysfuntionalities, such as cognitive deficits or impairment [*Scand. J. Psych.*, 43, 239-251, 2002; *Am. J. Psych.*, 158, 1722-1725, 2001].

Several neurotransmitters are presumed to be involved in the neuronal events regulating cognition. In particular, the cholinergic system plays a prominent role in cognition, and compounds affecting the cholinergic system are thus potentially useful for the treatment of cognitive impairment. Compounds affecting the 5-$HT_{1A}$ receptor and/or the 5-$HT_3$ receptor are known to affect the cholinergic system, and they may as such be useful in the treatment of cognitive impairment.

Hence, a compound exerting 5-$HT_{1A}$ and/or 5-$HT_3$ receptor activity would be expected to be useful in the treatment of cognitive impairment. A compound which moreover also exerts SERT activity would be particular useful for the treatment of cognitive impairment in depressed patients as such compound would also provide a fast onset of the treatment of the depression.

WO 03/029232 discloses e.g. the compound 1-[2-(2,4-dimethylphenyl-sulfanyl)phenyl]piperazine (example 1e) as a compound having SERT activity.

SUMMARY OF THE INVENTION

The present inventors have surprisingly found that 1-[2-(2,4-dimethylphenylsulfanyl)phenyl]piperazine exerts a combination of SERT inhibition, 5-$HT_3$ antagonism and 5-$HT_{1A}$ partial agonism. Accordingly, in one embodiment the present invention provides compound I which is 1-[2-(2,4-dimethylphenylsulfanyl)-phenyl]piperazine and pharmaceutically acceptable salts thereof, provided said compound is not the free base in a non-crystalline form.

In one embodiment, the invention provides the use of compound I in therapy.

In one embodiment, the invention provides a pharmaceutical composition comprising compound I.

In one embodiment, the invention provides therapeutic methods comprising the administration of an effective amount of compound I to a patient in need thereof.

In one embodiment, the invention provides the use of compound I in the manufacture of a medicament.

FIGURES

Figure 18A:
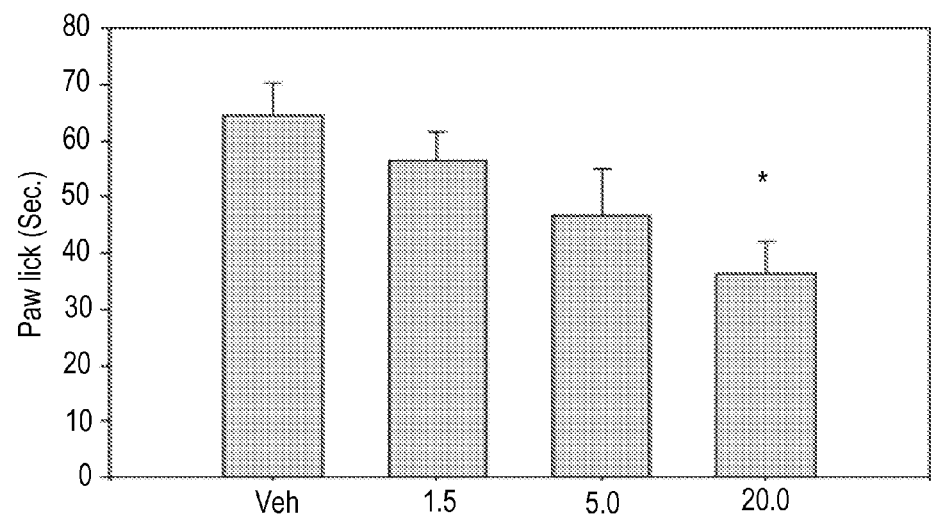
Figure 18B:
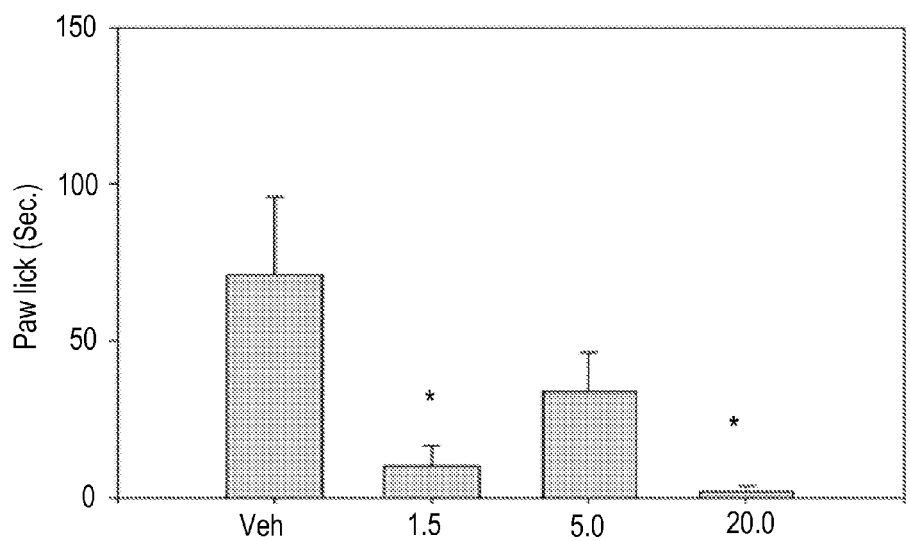
Figure 19A:
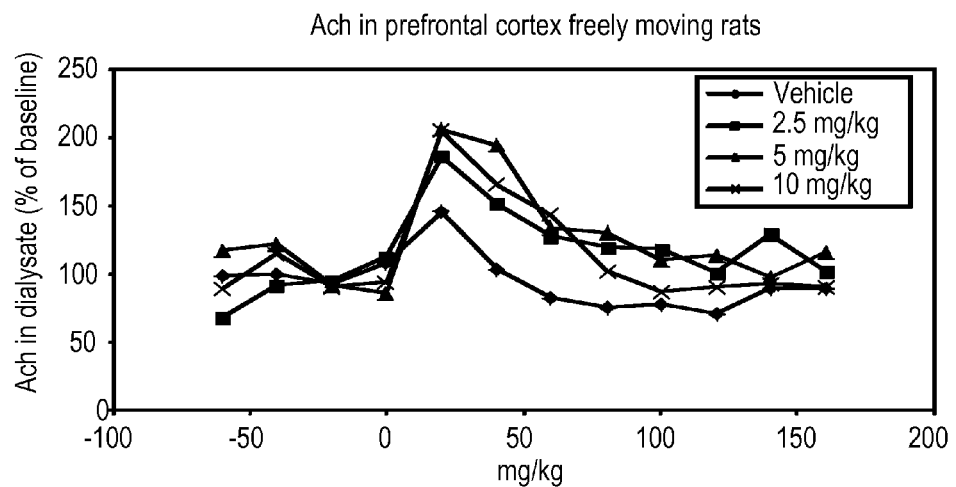
Figure 19B:
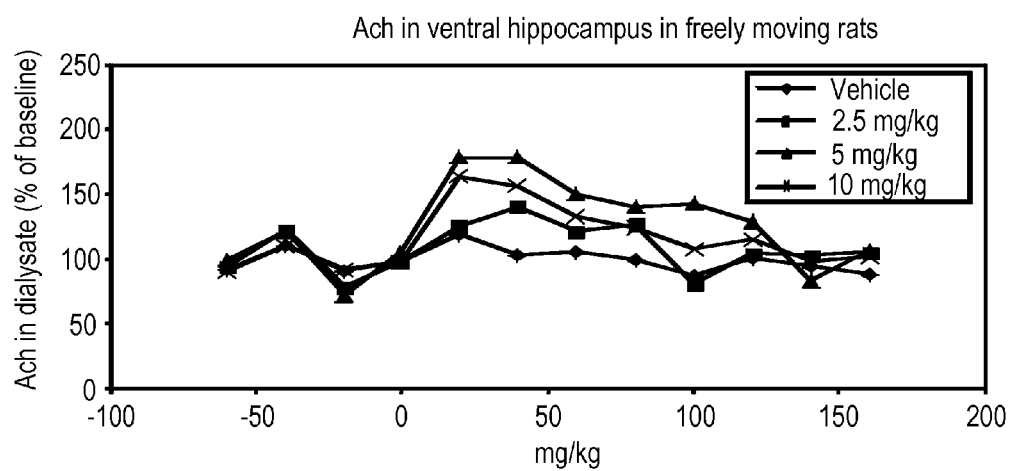
Figure 20:
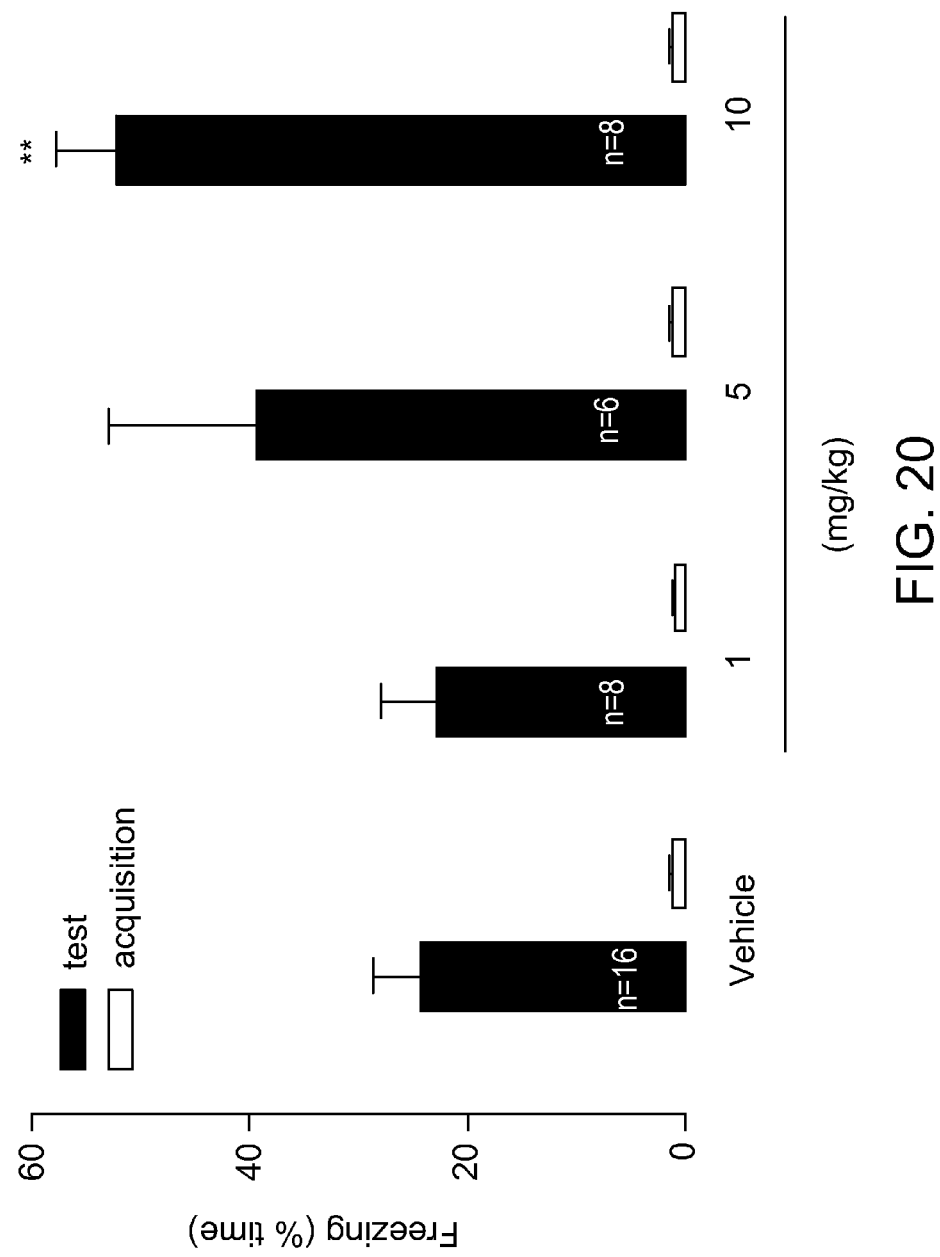
Figure 21:
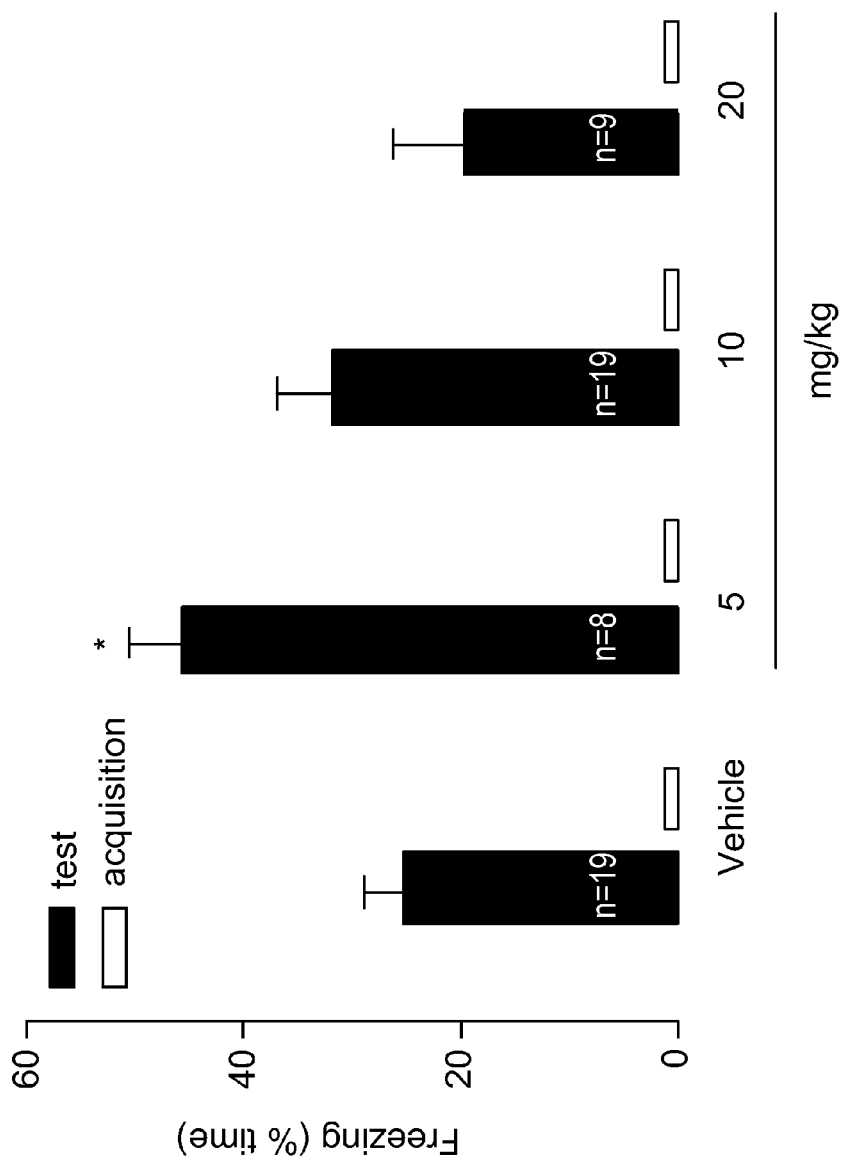
Figure 22:
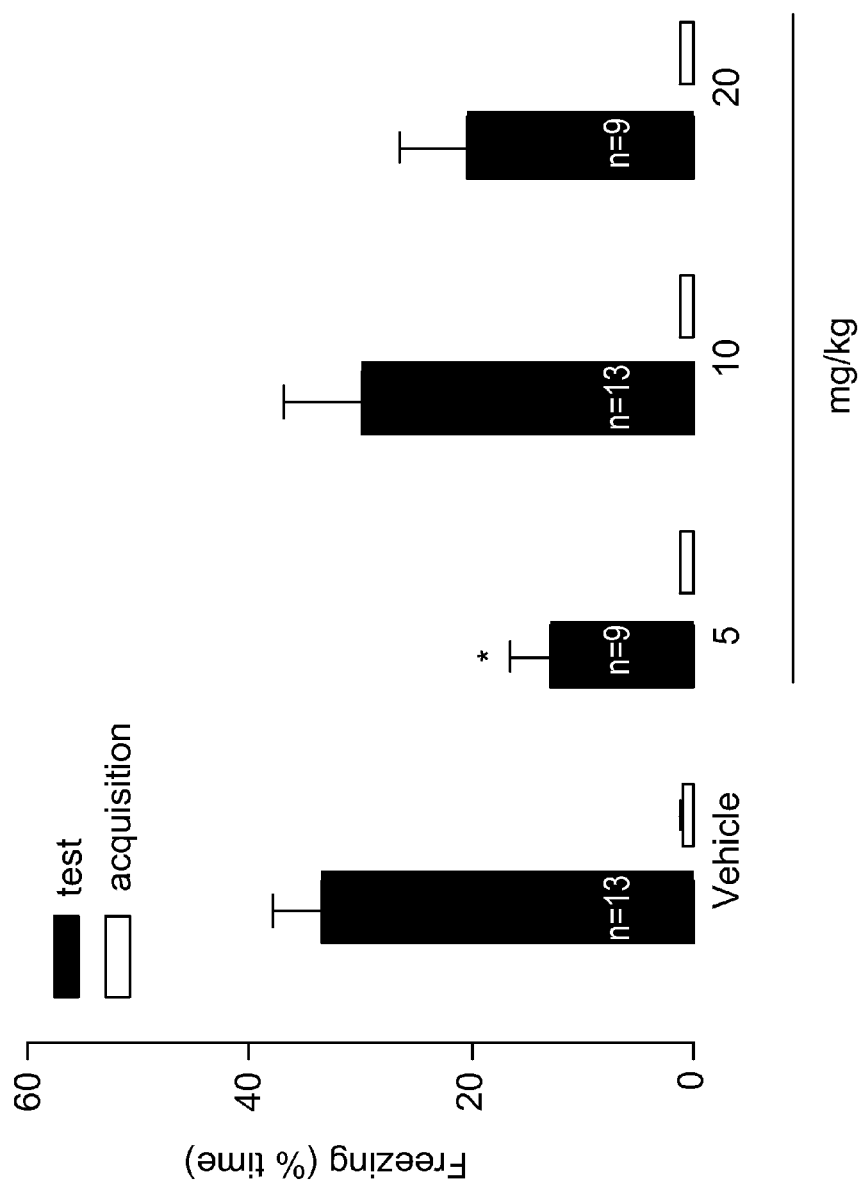

FIG. 1: XRPD of crystalline base
FIG. 2: XRPD of alpha form of hydrobromide salt
FIG. 3: XRPD of beta form of hydrobromide salt
FIG. 4: XRPD of gamma form of hydrobromide salt
FIG. 5: XRPD of hemi hydrate of hydrobromide salt
FIG. 6: XRPD of the mixture of the ethyl acetate solvate and the alpha form of the hydrobromide salt
FIG. 7: XRPD of hydrochloride salt
FIG. 8: XRPD of monohydrate of hydrochloride salt
FIG. 9: XRPD of mesylate salt
FIG. 10: XRPD of fumarate salt
FIG. 11: XRPD of maleate salt
FIG. 12: XRPD of meso-tartrate salt
FIG. 13: XRPD of L-(+)-tartrate salt
FIG. 14: XRPD of D-(−)-tartrate salt
FIG. 15: XRPD of sulphate salt FIG. 16: XRPD of phosphate salt
FIG. 17: XRPD of nitrate salt
FIGS. 18a and 18b: Effect of compounds of the present invention in the intradermal formalin test. X-axis shows the amount of compound administered; Y-axis shows the amount of time (sec) spent licking the paw. FIG. 18a: Response in the 0-5 minutes period; FIG. 18b: Response in the 20-30 minutes period.
FIG. 19a: Extra-cellular acetylcholine levels in prefrontal cortex in freely moving rats upon administration of 1-[2-(2, 4-dimethylphenylsulfanyl)phenyl]piperazine HBr salt.
FIG. 19b: Extra-cellular acetylcholine levels in ventral hippocampus in freely moving rats upon administration of 1-[2-(2,4-dimethylphenyl-sulfanyl)phenyl]piperazine HBr salt.
FIG. 20: Effect of 1-[2-(2,4-dimethylphenylsulfanyl)phenyl]piperazine HBr salt on contextual fear conditioning in Sprague-Dawley rats when given 60 minutes before acquisition. Freezing behaviour was scored during 58-s habituation period prior to the foot shock US (pre-shock acquisition) (white bars). Freezing behaviour was measured 24 h after the training (retention test) (black bars).
FIG. 21: Effect of 1-[2-(2,4-dimethylphenylsulfanyl)phenyl]piperazine HBr salt on contextual fear conditioning in Sprague-Dawley rats when given 1 h prior to the retention test. Freezing behaviour was scored during 58-s, prior to the foot shock US (acquisition) (white bars). Freezing behaviour was measured 24 h after the training (retention test) (black bars).
FIG. 22: Effect of AA21004 on contextual fear conditioning in Sprague-Dawley rats when given immediately after the acquisition. Freezing behaviour was scored during 58-s, prior to the foot shock US (pre-sock acquisition) (white bars). Freezing behaviour was measured 24 h after the training (retention test) (black bars).

DETAILED DESCRIPTION OF THE INVENTION

The invention relates to compound I, 1-[2-(2,4-dimethylphenylsulfanyl)-phenyl]piperazine, the structure of which is

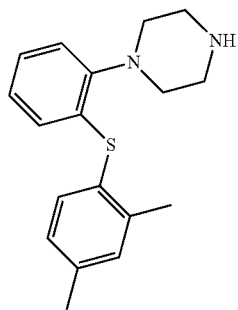 [SMILES: Cc1ccc(Sc2ccccc2N2CCNCC2)c(C)c1]

and pharmaceutically acceptable salts thereof provided compound I is not the free base in a non-crystalline form.

In one embodiment, said pharmaceutically acceptable salts are acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic salts, such as hydrochloric, hydrobromic, sulfuric, sulfamic, phosphoric and nitric acids. Particular mentioning is made of salts made from methanesulfonic acid, maleic acid, fumaric acid, meso-tartaric acid, (+)-tartaric acid, (−)-tartaric acid, hydrochloric acid, hydrobromic acid, sulphuric acid, phosphorous acid and nitric acid. Distinct mentioning is made of the hydrobromide salt.

Oral dosage forms, and in particular tablets, are often preferred by the patients and the medical practitioner due to the ease of administration and the consequent better compliance. For tablets, it is preferable that the active ingredients are crystalline. In one embodiment, the compounds of the present invention are crystalline.

In one embodiment the crystals of the present invention are solvates, i.e. crystals wherein solvent molecules from part of the crystal structure. The solvate may be formed from water, in which case the solvates are often referred to as hydrates. Alternatively, the solvates may be formed from other solvents, such as e.g. ethanol, acetone, or ethyl acetate. The exact amount of solvate often depends on the conditions. For instance, hydrates will typically loose water as the temperature is increased or as the relative humidity is decreased.

In one embodiment, the compounds of the present invention are unsolvated crystals.

Some compounds are hygroscopic, i.e. the absorb water when exposed to humidity. Hygroscopicity is generally regarded as an undesired property for compounds that are to be presented in a pharmaceutical formulation, in particular in a dry formulation, such as tablets. In one embodiment, the invention provides crystals with low hygroscopicity. For oral dosage forms using crystalline active ingredients it is also beneficial if said crystals are well-defined. In the present context, the term "well-defined" in particular means that the stoichiometry is well-defined, i.e. that the ratio between the ions forming the salt is the ratio between small integers, such as 1:1, 1:2, 2:1, 1:1:1, etc. In one embodiment, the compounds of the present invention are well-defined crystals.

The crystalline compounds of the present invention may exist in more than one form, i.e. they may exist in polymorphic forms. Polymorphic forms exist if a compound can crystallize in more than one form. The present invention is intended to encompass all such polymorphic forms, either as pure compounds or as mixtures thereof.

In one embodiment, the compounds of the present invention are in a purified form. The term "purified form" is intended to indicate that the compound is essentially free of other compounds or other forms of the same compound, as the case may be.

In one embodiment, the invention provides crystalline salts of compounds of the present invention with XRPD as shown in FIGS. 1-17, and in particular FIGS. 2, 3, 4 and 5.

The table below shows the major XRPD reflections for compounds of the present invention.
Selected X-ray peak positions (°2θ), All values+−0.1°

| | | | | |
|---|---|---|---|---|
| Crystalline base | 11.10 | 16.88 | 17.42 | 22.23 |
| hydrobromide (α) | 5.85 | 9.30 | 17.49 | 18.58 |
| hydrobromide (β) | 6.89 | 9.73 | 13.78 | 14.62 |
| hydrobromide (γ) | 11.82 | 16.01 | 17.22 | 18.84 |
| hydrobromide (hydrate) | 10.69 | 11.66 | 15.40 | 17.86 |
| hydrobromide (ethylacetate solvate) | 8.29 | 13.01 | 13.39 | 16.62 |
| hydrochloride | 9.41 | 12.37 | 19.66 | 22.55 |
| hydrochloride (monohydrate) | 7.72 | 13.45 | 15.39 | 17.10 |
| mesylate | 8.93 | 13.39 | 15.22 | 17.09 |
| hydrogenfumarate | 5.08 | 11.32 | 17.12 | 18.04 |
| hydrogenmaleate | 9.72 | 13.19 | 14.72 | 17.88 |
| mesohydrogentartrate | 9.51 | 10.17 | 16.10 | 25.58 |
| L-(+)-hydrogentartrate | 13.32 | 13.65 | 14.41 | 15.80 |

| | | | | |
|---|---|---|---|---|
| D-(–)-hydrogentartrate | 13.32 | 13.65 | 14.41 | 15.80 |
| hydrogen sulphate | 11.82 | 17.22 | 17.72 | 20.13 |
| dihydrogenphosphate | 7.91 | 11.83 | 15.69 | 17.24 |
| nitrate | 12.50 | 17.41 | 18.12 | 18.47 |

Figure 2:
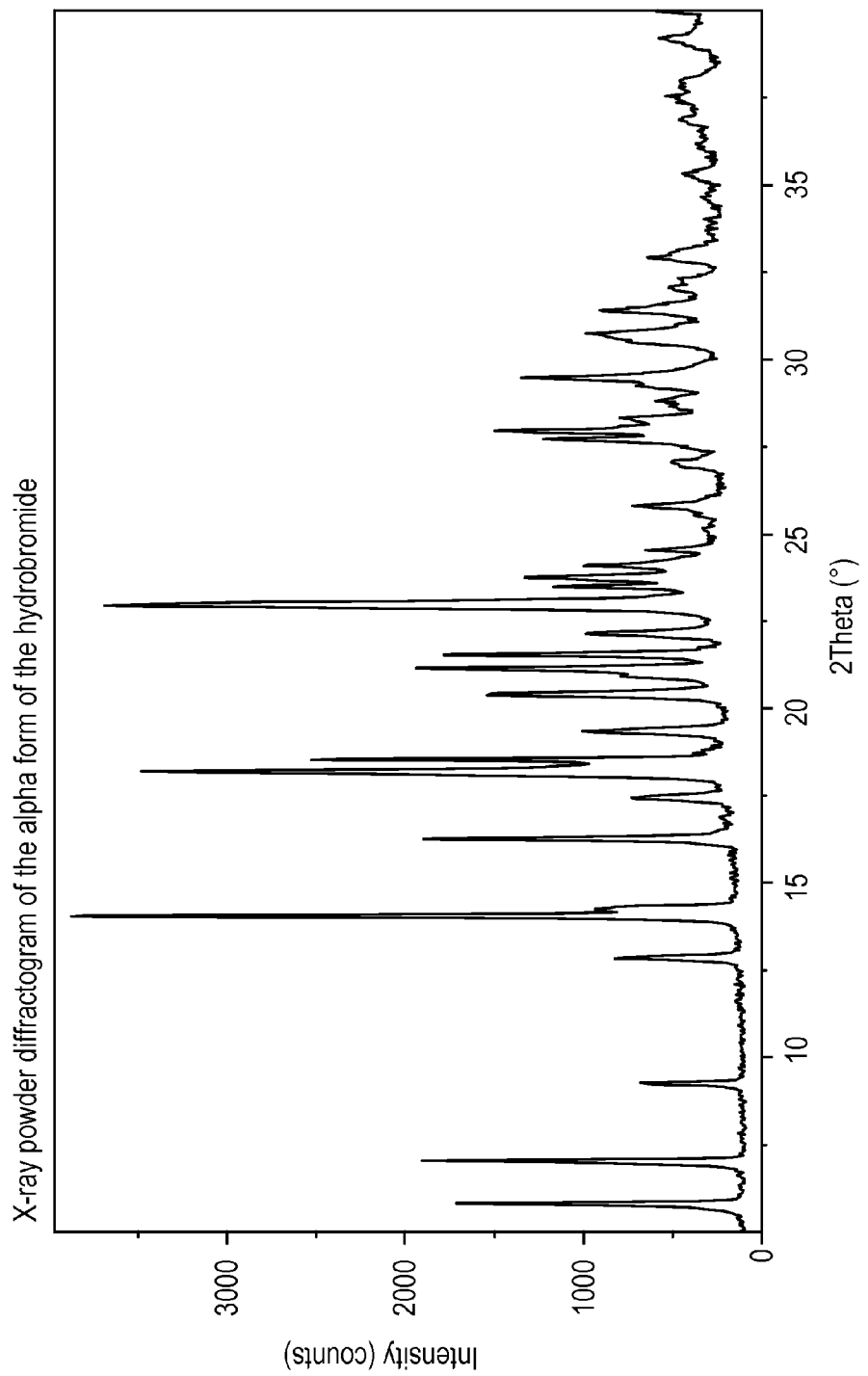
Figure 3:
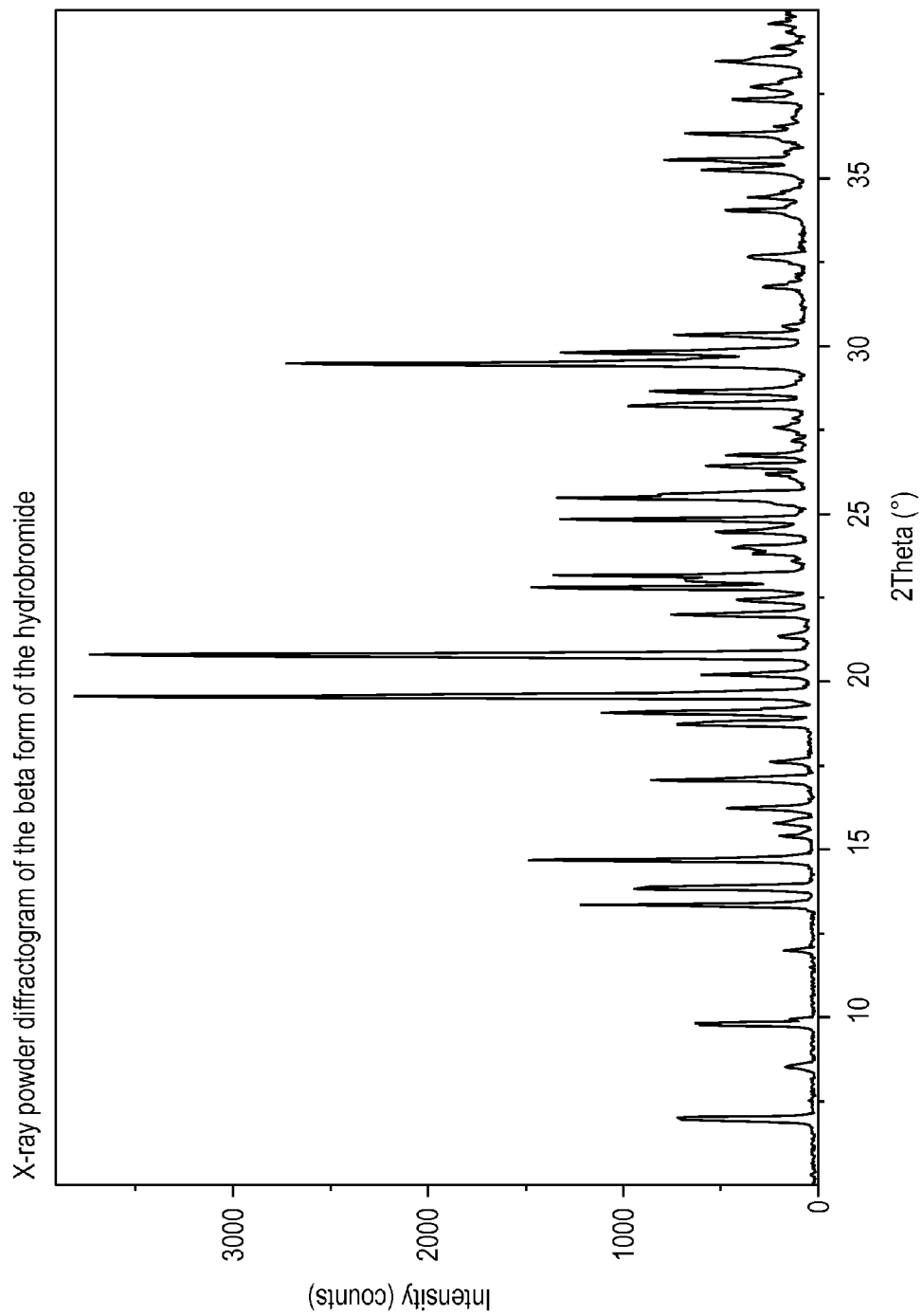

As evidenced, e.g., by FIGS. 2-5, compounds of the present invention, in casu the hydrobromide salt, may exist in several forms, i.e. be polymorphic. The polymorphic forms have different properties, and as shown in example 4d. The beta form of the hydrobromide salt is the more stable as demonstrated by the higher DSC melting point and the lower solubility. Moreover, the beta form has an attractive combination of low hygroscopicity and solubility, which makes this compound particular suited for making tablets. Hence, in one embodiment, the invention provides the hydrobromide salt of 1-[2-(2,4-dimethylphenylsulphanyl)-phenyl]piperazine with XRPD reflections at approximately 6.89, 9.73, 13.78 and 14.62 (°2θ), and in particular with an XRPD as shown in FIG. 3.

The solubility of an active ingredient is also of significance for the choice of dosage form as it may have a direct impact on bio-availability. For oral dosage forms, a higher solubility of the active ingredient is generally believed to be beneficial as it increases the bio-availability.

Cortical and hippocampal cholinergic neurotransmission are of great importance for cognition, and a number of preclinical observations point to the importance of the serotonin receptor 1A (5-$HT_{1A}$) for this system. T. Koyama in *Neurosci. Lett.*, 265, 33-36, 1999 reports that the 5-$HT_{1A}$ agonists BAYX3702 increases the acetylcholin efflux from the cortex and hippocampus in rats. Interestingly, the 5-$HT_{1A}$ antagonist WAY-100635 is capable of eliminating the effect of BAYX3702 showing that the effect of BAYX3702 is 5-$HT_{1A}$ mediated.

A number of studies have reported an effect of modulators of 5-$HT_{1A}$ on cognitive impairment. A. Meneses in *Neurobiol. Learn. Memory*, 71, 207-218, 1999 reports that the partial 5-$HT_{1A}$ agonist (±)-8-hydroxy-2-(di-n-propylamino)-tetralin, HCl (8-OH-DPAT) facilitates the consolidation of learning in normal rats and normalises cognitive functions in cognitively impaired rats.

These pre-clinical observations seem to be reflected in the clinic, too. T Sumiyoshi in *Am. J. Psych.*, 158, 1722-1725, 2001 reports a study wherein patients received typical antipsychotics, such as haloperidol, sulpride and pimozide, which all lack 5-$HT_{1A}$ activity in combination with placebo or tandospirone, which is a 5-$HT_{1A}$ agonist. Patients receiving tandospirone on top of the anti-psychotic showed an improvement in their cognitive performance whereas patients receiving placebo did not. Similarly, atypical anti-psychotics, such as clozapine, which are also 5-$HT_{1A}$ agonists enhance cognition in schizophrenic patients, whereas typical anti-psychotics, such as haloperidol which have no 5-$HT_{1A}$ activity, do not, Y. Chung, *Brain Res.*, 1023, 54-63, 2004.

As mentioned above, the cholinergic system is believed to be involved in the neuronal events regulating cognition, and the cholinergic system may be subject to an inhibitory control by the serotonin receptor 3 (5-$HT_3$) [(Giovannini et al, *J Pharmacol Exp Ther* 1998, 285:1219-1225; Costall and Naylor, *Current Drug Targets—CNS & Neurobiol Disord* 2004, 3:27-37)].

In a habituation test in mice, in a T-maze reinforced alternation task in rats, and in an object discrimination and reversal learning task in the marmoset, ondansetron reduced the impairment caused by the muscarinic antagonist, scopolamine or lesions of the cholinergic pathways emerging from the nucleus basalis (Barnes et al, *Pharamcol Biochem Behav* 1990, 35: 955-962; Carey et al, *Pharamcol Biochem Behav* 1992, 42: 75-83). Boast et al (*Neurobiol Learn Mem* 1999, 71: 259-271) used MK-801, a noncompetitive antagonist of the NMDA receptor, to disrupt the cognitive performance of rats trained on a delayed non-matching to sample radial maze task. Ondansetron was shown to block the cognitive impairment. Moreover, in a study on the amnesic effect of ethanol in a passive avoidance task in mice, this amnesic effect of ethanol was partially restored to normal by ondansetron (Napiorkowska-Pawlak et al, *Fundam Clin pharmacol* 2000, 14: 125-131). Thus, facilitation of the cholinergic transmission by 5-$HT_3$ antagonism after impairment of the cholinergic system in preclinical models (Diez-Ariza et al, *Psychopharmacology* 2003, 169: 35-41; Gil-Bea et al, *Neuropharmcol* 2004, 47: 225-232), suggests a basis for using this treatment in the therapy of cognitive disorders.

In a randomised double blind crossover study in healthy male subjects, assessments of verbal and spatial memory and sustained attention demonstrated that the 5-$HT_3$ antagonist, alosetron attenuated scopolamine induced deficits in verbal and spatial memory (Preston, *Recent Advances in the treatment of Neurodegenerative disorders and cognitive function*, 1994, (eds.) Racagni and Langer, Basel Karger, p. 89-93).

In conclusion, compounds exerting 5-$HT_{1A}$ partial agonistic activity in combination with 5-$HT_3$ antagonistic activity are believed to be particular useful for the treatment of cognitive impairment. Compounds which moreover exert serotonin reuptake inhibition would be particular useful for the treatment of cognitive impairment in association with depression as the serotonin reuptake inhibition in combination with the 5-$HT_{1A}$ partial agonism will lead to a faster onset of the effect of the treatment of the depression.

As shown in example 1, the compounds of the present invention are potent inhibitors of the human serotonin transporter, i.e. they inhibit serotonin reuptake. Moreover, the compounds are potent antagonists at the mouse, rat, guinea pig and canine 5-$HT_3$ receptor. At the human 5-$HT_3$ receptor, cloned into oocytes, the compounds were found to be antagonists at low concentrations ($IC_{50}$ approx. 30 nM), whilst at higher concentrations the compounds display agonistic properties ($ED_{50}$=2.1 µM). A subsequent application of compounds of the present invention at high concentration did not show any agonistic response, which could be due to rapid desenitisation or direct antagonism in vitro. Thus, at low concentrations compounds of the present invention display a marked antagonism at the human 5-$HT_3$ receptor as observed on the 5-$HT_3$ receptor from other species.

Compounds of the present invention bind with very low affinity to the 5-$HT_{1A}$ receptor in brain homogenate of both rats and mice. However, the compounds of the present invention bind to the human 5-$HT_{1A}$ receptor with a K, of 40 nM. Moreover, functional data show that the compounds of the present invention are partial agonists at the human 5-$HT_{1A}$ receptor, displaying an efficacy of 85%.

It is anticipated that the activity of the present invention at SERT, 5-$HT_3$-, and 5-$HT_{1A}$ receptors contribute to the in vivo profile of the compound in humans.

As shown in example 26 the compounds of the present invention give rise to an increase in the extra-cellular level of acetylcholine in the prefrontal cortex and the ventral hippocampus in rats. These pre-clinical findings are expected to translate into a clinical effect in the treatment of cognitive impairments, cf. the use of acetylcholine esterase inhibitors in the treatment of cognitive impairments, e.g. in Alzheimer's disease. Further support to this position can be found in example 27, wherein data show that compounds of the present invention enhances contextual memory in rats. All in all, the pharmacological profile of the compounds of the present invention combined with the effects on acetylcholine levels and memory in rats strongly suggest that the compounds of the present invention are useful in the treatment of cognitive impairment.

In one embodiment, the present invention relates to a method for the treatment of cognitive deficits or cognitive impairment, said method comprising the administration of a therapeutically effective amount of a compound of the present invention to a patient in need thereof.

Cognitive deficits or cognitive impairment include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive deficits or cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts. The terms "cognitive deficits" and "cognitive impairment" are intended to indicate the same and are used interchangeably.

In one embodiment, said patient is also diagnosed with another CNS disorder, such as affective disorders, such as depression; generalised depression; major depressive disorder; anxiety disorders including general anxiety disorder and panic disorder; obsessive compulsive disorder; schizophrenia; Parkinson's; dementia; AIDS dementia; ADHD; age associated memory impairment; or Alzheimer's.

Cognitive impairment is among the classic features of depression, such as e.g. major depressive disorder. Cognitive disorders may to some extent be secondary to depression in the sense that an improvement in the depressive state will also lead to an improvement of the cognitive impairment. However, there is also clear evidence that cognitive disorders are, indeed, independent from depression. For instance, studies have shown persistent cognitive impairment upon recovery from depression [*J. Nervous Mental Disease*, 185, 748-754, 197]. Moreover, the differential effect of antidepressants on depression and cognitive impairments lends further support to the notion that depression and cognitive impairment are independent, albeit often co-morbid conditions. While serotonin and noradrenalin medicaments provide comparable improvements in depressive symptoms, several studies have shown that modulation of the noradrenergic system does not improve the cognitive functions as much as serotonin modulation [*Brain Res. Bull.*, 58, 345-350, 2002; *Hum Psychpharmacol.*, 8, 41-47, 1993].

The treatment of cognitive impairment in depressed patients by the administration of the compounds of the present invention is believed to be particular advantageous. The multifaceted pharmacology of the compounds of the present invention, in particular the SERT, 5-HT$_3$ and 5-HT$_{1A}$ activity is expected to lead to improvement in cognitive functioning in combination with a fast onset treatment of the depressed state.

Cognitive impairment is a particularly important consideration in the elderly. Cognitive impairment normally increases with age, and further with depression. Hence, in one embodiment, the patient to be treated for cognitive impairment is elderly, and in particular elderly with depression.

Cognitive functions are, as mentioned above, often impaired in schizophrenic patients. Studies have also concluded that cognitive functioning is associated with vocational functioning in schizophrenia [*Scizophrenia Res.*, 45, 175-184, 2000]. In one embodiment, the patient to be treated for cognitive impairment is schizophrenic.

5-HT$_3$ receptor antagonists have additionally been suggested for the treatment of diseases such as emesis, chemotherapy-induced emesis, craving, substance abuse, pain, irritable bowel syndrome (IBS), schizophrenia, and eating disorders, [*Eur. J. Pharmacol.*, 560, 1-8, 2007; *Pharmacol. Therapeut.*, 111, 855-876, 2006; Alimentary Pharmacol. Ther., 24, 183-205, 2006]

Clinical studies show that a combination of mirtazipine and an SSRI are superior to SSRIs alone for the treatment of depressed patients with an inadequate clinical response (treatment resistant depression, TRD, or refractory depression) [*Psychother. Psychosom.*, 75, 139-153, 2006]. Mirtazapine is a 5-HT$_2$ and a 5-HT$_3$ antagonist, which lends support to the notion that compounds of the present invention are useful for the treatment of TRD.

Hot flushes are a symptom associated with the menopausal transition. Some women may suffer from this to an extent where it interferes with sleep or activities in general, and where treatment is necessary. Hormone replacement therapy with oestrogen has been established practice for decades, however, recently concerns have been voiced on side effects, such as breast cancer and cardiac events. Clinical trials with SSRIs have shown that these compounds have an effect on hot flushes, albeit less than for oestrogen [*J. Am. Med. Ass.*, 295, 2057-2071, 2006]. Treatment of hot flushes with compounds inhibiting serotonin reuptake, e.g. compounds of the present invention could, however, be an alternative treatment for women who can not or will not accept oestrogen.

Sleep apnoea or obstructive sleep apnoea-hyponea syndrome or obstructive sleep-disordered breathing is a disorder for which an effective pharmacotherapy remains to be identified. Several studies in animals, however, suggest that 5-HT$_3$ antagonists, e.g. compounds of the present invention may be effective in the treatment of these diseases[*Sleep*, 21, 131-136, 1998; Sleep, 8, 871, 878, 2001].

In one embodiment, the invention relates to a method of treating a disease selected from affective disorders, depression, major depressive disorder, postnatal depression, depression associated with bipolar disorder, Alzheimer's disease, psychosis, cancer, age or Parkinson's disease, anxiety, general anxiety disorder, social anxiety disorder, obsessive compulsive disorder, panic disorder, panic attacks, phobia, social phobia, agoraphobia, stress urinary incontinence, emesis, IBS, eating disorders, chronic pain, partial responders, treatment resistant depression, Alzheimer's disease, cognitive impairment, ADHD, melancholia, PTSD, hot flushes, sleep apnoea, alcohol, nicotine or carbohydrate craving, substance abuse and alcohol or drug abuse, the method comprising the administration of a therapeutically effective amount of a compound of the present invention to a patient in need thereof. In one embodiment, said patient being treated for any of the above listed diseases has initially been diagnosed with said disease.

It is well know that treatment with anti-depressants in general and SSRI's in particular may be associated with sexual dysfunction and which frequently leads to discontinuation of the treatment. As much as 30-70% of patients on SSRIs report deficits in sexual function [*J. Clin. Psych.*, 66, 844-848, 2005], which deficits include decreased libido, delayed, reduced or absent orgasms, diminished arousal, and erectile dysfunction. A total of 114 subjects have been exposed to compounds of the present invention in clinical trials; of these 114 subjects, only one subject reported sexual dysfunction. These data suggest that clinical intervention using compounds of the present invention is associated with surprisingly few deficits in sexual functioning.

As mentioned above, compounds of the present invention are particularly well suited for the treatment of chronic pain. Chronic pain includes indications such as phantom limb pain, neuropathic pain, diabetic neuropathy, post-herpetic neuralgia (PHN), carpal tunnel syndrome (CTS), HIV neuropathy, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, tension-type headache, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain or geriatric pain.

Data presented in example 16 shows that compounds of the present invention are useful in the treatment of pain, and that they may even have an analgesic effect, additionally studies in an animal model of neuropathic pain confirm this observation.

A "therapeutically effective amount" of a compound as used herein means an amount sufficient to cure, alleviate or partially arrest the clinical manifestations of a given disease and its complications in a therapeutic intervention comprising the administration of said compound. An amount adequate to accomplish this is defined as "a therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatment are two separate aspects of the invention. The patient to be treated is preferably a mammal, in particular a human being.

Typically, the treatment of the present invention will involve daily administration of the compounds of the present invention. This may involve once daily administration, or administration twice a day or even more frequently.

In one embodiment, the invention relates to the use of a compound of the present invention for the manufacture of a medicament for the treatment of affective disorders, depression, major depressive disorder, postnatal depression, depression associated with bipolar disorder, Alzheimer's disease, psychosis, cancer, age or Parkinson's disease, anxiety, general anxiety disorder, social anxiety disorder, obsessive compulsive disorder, panic disorder, panic attacks, phobia, social phobia, agoraphobia, stress urinary incontinence, emesis, IBS, eating disorders, chronic pain, partial responders, treatment resistant depression, Alzheimer's disease, cognitive impairment, ADHD, melancholia, PTSD, hot flushes, sleep apnoea, alcohol, nicotine or carbohydrate craving substance abuse, or alcohol or drug abuse.

In one embodiment, the invention relates to compounds of the present inventions for use in the treatment of a disease selected from affective disorders, depression, major depressive disorder, postnatal depression, depression associated with bipolar disorder, Alzheimer's disease, psychosis, cancer, age or Parkinson's disease, anxiety, general anxiety disorder, social anxiety disorder, obsessive compulsive disorder, panic disorder, panic attacks, phobia, social phobia, agoraphobia, stress urinary incontinence, emesis, IBS, eating disorders, chronic pain, partial responders, treatment resistant depression, Alzheimer's disease, cognitive impairment, ADHD, melancholia, PTSD, hot flushes, sleep apnea, alcohol, nicotine or carbohydrate craving, substance abuse, and alcohol and drug abuse.

The effect of the compounds of the present invention on cognition in humans may be evaluated in a number of ways. The effect may be evaluated in tests wherein healthy volunteers are administered the compound followed by a measurement of the cognitive performance in recognised tests, such as e.g. Auditory Verbal Learning Test (AVLT), Wisconsin Card Sorting Test (WCST), or sustained attention, [*Psycopharmacol*, 163, 106-110, 2002; *Psychiatry Clin. Neurosci.*, 60, 70-76, 2006]. The effect may of course also be assessed in patients suffering from cognitive impairment using the same sort of tests. Alternatively, cognitive models may be used wherein cognitive impairment is induced in healthy volunteers and wherein a restorative effect of the compounds of the present invention is measured. Cognitive impairment may be induced by e.g. scopolamine, sleep deprivation, alcohol, and tryptophane depletion.

The pharmaceutical formulations of the invention may be prepared by conventional methods in the art. Particular mentioning is made of tablets, which may be prepared by mixing the active ingredient with ordinary adjuvants and/or diluents and subsequently compressing the mixture in a conventional tabletting machine. Examples of adjuvants or diluents comprise: anhydrous calcium hydrogen phosphate, PVP, PVP-VA co-polymers, microcrystalline cellulose, sodium starch glycolate, corn starch, mannitol, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 1 to 50 mg. An upper limit is believed to be set by the concentration dependency of the 5-HT$_3$ activity. The total daily dose is usually in the range of about 1-20 mg, such as about 1 to 10 mg, about 5-10 mg, about 10-20 mg, or about 10-15 mg of the compound of the invention. Particular mentioning is made of daily doses of 5, 10, 15 or 20 mg.

Tablets comprising a compound of the present invention may conveniently be prepared by wet granulation. Using this method, the dry solids (active ingredients, filler, binder etc.) are blended and moistened with water or another wetting agent (e.g. an alcohol) and agglomerates or granules are built up of the moistened solids. Wet massing is continued until a desired homogenous particle size has been achieved whereupon the granulated product is dried. The compounds of the present invention are typically mixed with lactose monohydrate, corn starch and copovidone in a high shear mixer together with water. Following formation of granulates, these granulates may be sieved in a sieve with a suitable sieve size, and dried. The resulting, dried granulates are then mixed with microcrystalline cellulose, croscarmellose sodium and magnesium stearate, following which the tablets are pressed. Alternatively, wet granulation of the compounds of the present invention may be achieved using mannitol, corn starch and copovidone, which granulates are mixed with microcrystalline cellulose, sodium starch glycolate and magnesium stearate before tablets are pressed. Alternatively, wet granulation of the compounds of the present invention may be achieved by using anhydrous calcium hydrogen phosphate, corn starch and copovidone, which granulates are mixed with microcrystalline cellulose, sodium starch glycolate (type A), talc and magnesium stearate before tablets are pressed. Copovidone is a PVP-VA copolymer.

In one embodiment, the compound of the present invention is the hydrobromide salt, e.g. in the beta form, and suitable tablets may be composed as follows—percentages indicated are w/w-%

| | |
|---|---|
| HBr salt | 2-20% |
| Lactose monohydrate | 30-50% |
| Starch | 15-30% |
| Copovidone | 3-5% |
| Microcrystalline cellulose | 15-25% |
| Croscarmellose sodium | 2-5% |
| Mg stearate | 0.5-5% |

In particular, the tablets may be composed as follows

| | |
|---|---|
| HBr salt | 3-4% |
| Lactose monohydrate | 44-46% |
| Starch | 22-23% |
| Copovidone | 3-4% |
| Microcrystalline cellulose | 20-22% |
| Croscarmellose sodium | 3-3.5% |
| Mg stearate | 0.5-1% | or

| | |
|---|---|
| HBr salt | 15-16% |
| Lactose monohydrate | 35-38% |
| Starch | 18-20% |
| Copovidone | 3-4% |
| Microcrystalline cellulose | 20-22% |
| Croscarmellose sodium | 3-3.5% |
| Mg stearate | 0.5-1% | or

| | |
|---|---|
| HBr salt | 1-2% |
| Lactose monohydrate | 44-46% |
| Starch | 20-24% |
| Copovidone | 3-4% |
| Microcrystalline cellulose | 22-24% |
| Croscarmellose sodium | 3-4% |
| Mg stearate | 0.5-1% |

In one embodiment, the compound of the present invention is the hydrobromide salt, e.g. in the beta form, and suitable tablets may be composed as follows

| | |
|---|---|
| HBr salt | 2-30% |
| Mannitol | 25-45% |
| Corn starch | 10-20% |
| Copovidone | 2-4% |
| Microcrystalline cellulose | 22-27% |
| Sodium starch glycolate | 4-5% |
| Mg stearate | 0.25-5%, such as 0.25-2% |

In particular, the tablets may be composed as follows

| | |
|---|---|
| HBr salt | 20-22% |
| Mannitol | 35-36% |
| Corn starch | 10-12% |
| Copovidone | 2.5-3% |
| Microcrystalline cellulose | 24-25% |
| Sodium starch glycolate | 3-4% |
| Mg stearate | 0.25-1% | or

| | |
|---|---|
| HBr salt | 12-13% |
| Mannitol | 36-37% |
| Corn starch | 18-19% |
| Copovidone | 3-4% |
| Microcrystalline cellulose | 24-25% |
| Sodium starch glycolate | 3-4% |
| Mg stearate | 0.25-1% | or

| | |
|---|---|
| HBr salt | 25-27% |
| Mannitol | 27-29% |
| Corn starch | 13-15% |
| Copovidone | 3-4% |
| Microcrystalline cellulose | 24-25% |
| Sodium starch glycolate | 3-5% |
| Mg stearate | 0.25-1% | or

| | |
|---|---|
| HBr salt | 3-4% |
| Mannitol | 40-42% |
| Corn starch | 20-22% |
| Copovidone | 3-4% |
| Microcrystalline cellulose | 26-28% |
| Sodium starch glycolate | 3-5% |
| Mg stearate | 0.5% |

In one embodiment, the compound of the present invention is the hydrobromide salt and suitable tablets may be composed as follows

| | |
|---|---|
| HBr salt | 3-8% |
| Anhydrous calcium hydrogen phosphate | 35-45% |
| Corn starch | 15-25% |
| Copovidone | 2-6% |
| Microcrystalline cellulose | 20-30% |
| Sodium starch glycolate | 1-3% |
| Talc | 2-6% |
| Magnesium stearate | 0.5-2% |

In particular, the tablets may be composed as follows

| | |
|---|---|
| HBr salt | approximately 5% |
| Anhydrous calcium hydrogen phosphate | approximately 39% |
| Corn starch | approximately 20% |
| Copovidone | approximately 3% |
| Microcrystalline cellulose | approximately 25% |
| Sodium starch glycolate | approximately 3% |
| Talc | approximately 4% |
| Magnesium stearate | approximately 1% |

Tablets with different amounts of active compound, such as corresponding to e.g. 2.5, 5, 10, 20, 25, 30, 40, 50, 60 or 80 mg of the free base may be obtained by choosing the right amount of the compound of the present invention in combination with a tablet of an appropriate size.

The size of the crystals used for preparing tablets comprising compounds of the present invention are of significance. If the crystals are too small they may stick to the plunger in the tablet machines. On the other hand, they cannot be too large either. The dissolution rate in the intestines decrease when crystal size increases. Hence, if the crystals are too large it may compromise the bioavailability of the compounds. Particle size distribution may be described using quantiles, e.g. D5%, D10%, D50%, D90%, D95% and D98%. As used herein, "particle size distribution" means the cumulative volume size distribution of equivalent spherical diameters as determined by laser diffraction at 1 bar dispersive pressure in a Sympatec Helos equipment.

In one embodiment, the crystals of the compound of the present invention, and in particular the beta from of the hydrobromide salt have a particle size distribution corresponding to D98%: 650-680 µm; D50%: 230-250 µm; and D5%: 40-60 µm. In a further embodiment, the particle size distribution corresponds to D98%: 370-390; d50%: 100-120 µm; D5%: 5-15 µm. In a still further embodiment, the particle size distribution corresponds to D98%: 100-125 µm; D50%: 15-25 µm; and D5%: 1-3 µm. In an even further embodiment, the particle size distribution corresponds to D98%: 50-70 µm; D50%: 3-7 µm; and D5%: 0.5-2.

The free base of the present invention may be prepared as disclosed in WO 2003/029232. Salts of the present invention may be prepared by dissolving the free base in an appropriate solvent, adding the relevant acid, followed by precipitation. Precipitation may be accomplished either by the addition of a second solvent, and/or evaporation, and/or cooling. Alternatively, the free base of the present invention and ultimately the compounds of the present invention may be synthesised in a palladium catalysed reaction as described below.

Formation of aromatic carbon-heteroatom bonds may be achieved by nucleophilic aromatic substitution or copper-mediated Ullman reactions. More recently, palladium has been shown to be a powerful catalyst for the formation of such bonds, and in particular the formation of C—N and C—S bonds, see e.g. U.S. Pat. No. 5,573,460.

In one embodiment, the invention provides a process for the preparation of

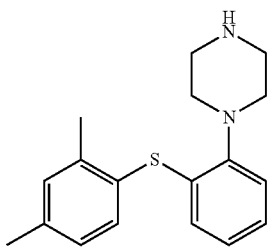 [SMILES: Cc1ccc(Sc2ccccc2N2CCNCC2)c(C)c1]

the process comprising reacting compound II

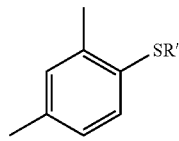

[II]

wherein R' represents hydrogen or a mono-valent metal ion, with a compound of formula III

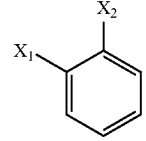

[III]

wherein $X_1$ and $X_2$ independently represent halogen, and a compound of formula IV

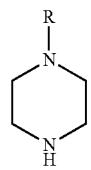

[IV]

wherein R represents hydrogen or a protecting group, in the presence of a solvent, a base and a palladium catalyst consisting of a palladium source and a phosphine ligand at a temperature between 60° C. and 130° C.

In one embodiment, the process is divided in sub-processes wherein compound II and compound III are reacted in a first reaction to provide a compound of the formula

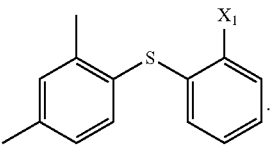

This compound is then optionally purified to a suitable degree before being reacted with compound IV to provide 4-[2-(2, 4-dimethyl-phenylsulfanyl)-phenyl]-piperazine.

One-pot syntheses, i.e. syntheses wherein all reactants are mixed together at the start of the reaction or process, are particularly useful due to their inherent simplicity. On the other hand, the number of possible unwanted side-reactions is dramatically increased, which again means that the number and/or the amount of unwanted side products may increase and the yield of the desired product decrease correspondingly. For the present process in particular, it may be observed that piperazine has two nitrogens each of which could potentially participate in the formation of a C—N bond. It has surprisingly been found that the present process may be run as a one-pot synthesis, i.e. a process wherein compound II, compound III and compound VI are mixed from the beginning, while maintaining a high yield of a pure compound.

Compound II is a thiol or the corresponding thiolate. From a occupational health perspective is may be beneficial to use a thiolate, such as the Li+, Na+ or K+ thiolate to avoid the odour problems associated with thiols. Nonetheless, in one embodiment, R' is hydrogen.

Compound III is a 1,2-dihalogen activated benzene, and the halogens may be any of Cl, Br and I. In particular, compound II is 1-bromo-2-iodo-benzene or 1,2-dibromo-benzene.

The solvent used in the process of the present invention may be selected from aprotic organic solvents or mixtures of such solvents with a boiling temperature within the reaction temperature range, i.e. 60-130° C. Typically, the solvent is selected from amongst toluene, xylene, triethyl amine, tributyl amine, dioxan, N-methylpyrrolidone, or from any mixture thereof. Particular mentioning is made of toluene as solvent.

Central to the present process is the use of a palladium catalyst without which the reactions do not take place. The palladium catalyst consists of a palladium source and a phosphine ligand. Useful palladium sources include palladium in different oxidations states, such as e.g. 0 and II. Examples of palladium sources which may be used in the process of the present invention are $Pd_2dba_3$, $Pddba_2$ and $Pd(OAc)_2$. dba abbreviates dibenzylideneacetone. Particular mentioning is made of $Pddba_2$ and $Pd_2dba_3$. The palladium source is typically applied in an amount of 0.1-10 mole-%, such as 1-10 mole-%, such as 1-5 mole-%. Throughout this application, mole-% is calculated with respect to the limiting reactant.

Numerous phosphine ligands are known, both monodentate and bidentate. Useful phosphine ligands include racemic 2,2'-bis-diphenylphosphanyl-[1,1']binaphtalenyl (rac-BINAP), 1,1'-bis(diphenylphosphino)ferrocene (DPPF), bis-(2-diphenylphosphinophenyl)ether (DPEphos), tri-t-butyl phosphine (Fu's salt), biphenyl-2-yl-di-t-butyl-phosphine, biphenyl-2-yl-dicyclohexyl-phosphine, (2'-dicyclohexylphosphanyl-biphenyl-2-yl)-dimethyl-amine, [2'-(di-t-butyl-phosphanyl)-biphenyl-2-yl]-dimethyl-amine, and dicyclohexyl-(2',4',6'-tri-propyl-biphenyl-2-yl)-phosphane. Moreover, carbene ligands, such as e.g. 1,3-bis-(2,6-di-iso-propyl-phenyl)-3H-imidazol-1-ium; chloride may be used instead of phosphine ligands. In one embodiment, the phosphine ligand is rac-BINAP, DPPF or DPEphos, and in particular rac-BINAP. The phosphine ligand is usually applied in an amount between 0.1 and 10 mole-%, such as 1 and 5 mole-%, typically around 1-2 mole-%.

Base is added to the reaction mixture to increase pH. In particular bases selected from NaOt-Bu, KOt-Bu and $Cs_2CO_3$ are useful. Organic bases, such as 1,8-diazabicyclo[5.4.0] undec-7-ene (DBU) and 1,4-diazabicyclo[2.2.2]octane (DABCO) may be applied as well. Particular mentioning is made of NaO(t-Bu) and KO(t-Bu). Typically, the base is added is an amount around 1-5 equivalents, such as 1-3 equivalents, such as 2-3 equivalents.

Compound IV is a piperazine compound. Piperazine has two nitrogens, only one of which is to participate in the C—N bond formation. In one embodiment, formation of bonds to the second nitrogen is avoided by using a mono-protected piperazine, i.e. an embodiment wherein R is a protective group. Many protective groups are known in the art, and useful examples include boc, Bn, Cbz, C(=O)OEt and Me, and in particular boc. Bn abbreviates benzyl; boc abbreviates t-butyloxycarbonyl; and cbz abbreviates benzyloxycarbonyl. If a protected piperazine is used in the reactions, the protecting group has to be removed in a subsequent step, typically by the addition of aqueous acid. If methyl is used as the protecting group, the methyl may be removed in a reaction with carbamate and subsequent removal of this group.

It has surprisingly been found that unprotected piperazine may be used as well without the formation of unwanted bonds to the second nitrogen. Protected and unprotected piperazine have different solubilities in different solvents; as an example, piperazine is practically insoluble in toluene whereas boc protected piperazine is highly soluble in toluene. Normally it would be expected that it is a requirement for a successful reaction that all reactants are readily soluble in the applied solvent. Nevertheless, it has been found that the process of the present invention runs with a high yield with toluene as solvent and with unprotected piperazine, i.e. in an embodiment wherein R is hydrogen. Hence, in one embodiment, the solvent is toluene and compound IV is piperazine. In a further embodiment, this combination of conditions is used in a one-pot synthesis.

In one embodiment, the temperature under which to run to process is approximately 80° C.-approximately 120° C.

In one embodiment, 1-[2-(2,4-dimethyl-phenylsulfanyl) phenyl]-piperazine is prepared in a process comprising the following steps
  a. Dissolving or dispersing 1-1.5 equivalents of compounds II, III and IV in toluene to obtain mixture A;
  b. Adding 1-2 mole-% of $Pddba_2$ and 1-2 mole-% of rac-BINAP together with 2-3 equivalents of NaOt-Bu, optionally dispersed or dissolved or dispersed in toluene, to mixture A to obtain mixture B, which is heated to around 100° C. until compound II and III are fully converted, typically 5-10 hours;
  c. Increasing the temperature of the mixture obtained in step b to around 120° C. until compound IV is fully converted, typically 16-32 hours; and
  d. Optionally removing the protecting group by the addition of aqueous acid if compound III is a protected piperazine.
  Optionally, purifications steps may be included in the above sequence of reaction steps.

In one embodiment, 1-1.5 equivalents of 2,4-dimethyl-thiol, 1-bromo-2-iodo benzene (or 1,2-dibromo-benzene) and piperazine is dispersed in toluene followed by the addition of 2-5, such as 3 equivalents NaOt-Bu and 1-2 Mole-% $Pd_2dba_3$ and rac-BINAP dispersed in toluene to obtain a mixture which is refluxed for 2-10 hours, typically 3-5 hours to obtain 1-[2-(2,4-dimethyl-phenylsulfanyl)-phenyl]-piperazine. Optionally, this product may be further reacted with aqueous HBr to achieve the corresponding hydrobromic acid addition salt.

In one embodiment, 2-5 equivalents of NaOt-Bu, 2-5 equivalents piperazine, 0.2-0.6 mole-% $Pddba_2$, and 0.6-1 mole-% rac-BINAP is dispersed in toluene to obtain mixture A', to which mixture approximately 1 equivalent 2-bromo-iodobenzene is added to obtain mixture B', to which mixture 1 equivalent 2,4-dimethylthiophenol is added and the resulting mixture is heated to reflux for 3-7 hours, such as 4-6 hours to obtain 1-[2-(2,4-dimethyl-phenylsulfanyl)-phenyl]-piperazine. Optionally, this product may be further reacted with aqueous HBr to achieve the corresponding hydrobromic acid addition salt.

In some situations it may be desirable to obtain an acid addition salt of 1-[2-(2,4-Dimethyl-phenylsulfanyl)-phenyl]-piperazine rather than the free base. Acid addition salts may be achieved in a further process step in which the free base obtained is reacted with a relevant acid, such as e.g. fumaric acid, sulphuric acid, hydrochloric acid or hydrobromic acid. The acid may be added directly to the reaction mixture or, alternatively, the free base may be purified to any suitable degree initially before such step. If the free base has been isolated as a dry compound, it may be necessary to use a solvent in order to bring the free base into solution prior to a reaction with the acid. In one embodiment, aqueous hydrobromic acid is added directly to the reaction mixture without any initial purification of the free base.

In processes wherein a protected piperazine has been used, the protecting group has to be removed by the addition of an aqueous acid as explained above. In one embodiment, said aqueous acid may be selected to achieve two transformations, i.e. the de-protection of the protected piperazine and the formation of an acid addition salt. In particular, aqueous hydrobromic acid may be used to de-protect protected piperazine and to obtain the hydrobromic acid addition salt in one process step.

It goes for all the reactions and reaction mixtures mentioned here that it may be an advantage to purge them with an inert gas or run them under a blanket of inert gas. Nitrogen is a cheap and readily available example of an inert gas All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Analytical Methods $^1$H NMR spectra are recorded at 500.13 MHz on a Bruker Avance DRX500 instrument. Dimethyl sulfoxide (99.8% D) is used as solvent, and tetramethylsilane (TMS) is used as internal reference standard.

The melting points are measured using Differential Scanning calorimetry (DSC). The equipment is a TA-Instruments DSC-Q1000 calibrated at 5°/min to give the melting point as onset value. About 2 mg of sample is heated 5°/min in a loosely closed pan under nitrogen flow.

Thermo gravimetric analysis (TGA) used for estimation of solvent/water content of dried material is performed using a TA-instruments TGA-Q500. 1-10 mg sample is heated 10°/min in an open pan under nitrogen flow.

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector.

Example 1

In Vitro Receptor Pharmacology

Rat serotonin transporter: IC$_{50}$ 5.3 nM (blockade of 5-HT uptake)

Human serotonin transporter: IC$_{50}$ 40 nM (blockade of 5-HT uptake)

Human 5-HT$_{1A}$ receptor: K$_i$ 40 nM with partial agonism (efficacy 85%)

Rat 5-HT$_3$ receptor: IC$_{50}$ 0.2 nM (antagonism in functional assay)

Human 5-HT$_{3A}$ receptor: IC$_{50}$ around 20 nM (antagonism in functional assay). At higher concentration, the compound exhibits agonistic activity with an ED$_{50}$ of 2.1 μM. The compound of the invention also showed high affinity for the human 5HT3 receptor in an in vitro binding assay (Ki 4.5 nM).

Example 2

Cognitive Effects

As discussed above, the compounds of the present invention interact with the cholinergic system, and it would be expected to see an effect in one or more of the following in vivo models.

Five choice serial reaction time test (5-CSRT), which is useful for demonstrating an effect on continuous attention Spatial Y maze test, which is useful for demonstrating effects on short, long-term and working memory Attentional set shifting model, which is useful for demonstrating effects on executive functioning, i.e. reasoning and problem solving Example 3a Preparation of the Free Base of Compound I 10 grams of 1-[2-(2,4-Dimethylphenylsulfanyl)-phenyl] piperazine hydrobromide was treated with a stirred mixture of 100 ml 3 M NaOH and 100 ml ethyl acetate for 10 minutes. The organic phase was separated, washed with 100 ml 15%-wt NaCl (aq), dried over MgSO$_4$, filtered and concentrated in vacuum producing 7.7 gram (98%) of compound I base as a clear colourless oil.

NMR complies with structure.

Example 3b

Preparation of Crystalline Base of Compound I 3.0 gram of 1-[2-(2,4-Dimethylphenylsulfanyl)-phenyl] piperazine colourless oil was treated with 70 ml acetonitrile and heated to reflux. The almost clear solution was filtered and the clear filtrate was cooled spontaneously upon which precipitation began shortly after filtration. The mixture was stirred at room temperature (22° C.) for 2 hours and the product was isolated by filtration and dried in vacuum (40° C.) overnight. The crystalline base was isolated as a white solid in 2.7 gram (90%). NMR complies with structure. Elemental analysis: 72.40%; C, 9.28%; N, 7.58%; H (theory: 72.26%; C, 9.36%; N, 7.42%; H)

Example 3c

Characterisation of Crystalline Base of Compound I

The base, as prepared in example 3b, is crystalline (XRPD)—see FIG. 1. It has a melting point of ~117° C. It is not hygroscopic and has a solubility of 0.1 mg/ml in water.

Example 4a

Preparation of the Alpha Form of the Hydrobromide Salt of Compound I 2.0 gram of 1-[2-(2,4-Dimethylphenylsulfanyl)-phenyl]piperazine was dissolved in hot 30 ml ethyl acetate and added 0.73 ml 48%-wt HBr (aq). This addition caused formation of a thick slurry and additional 10 ml ethyl acetate was added in order to have proper stirring. The slurry was stirred at room temperature for one hour. Filtration and drying in vacuum (20° C.) over night produced 2.0 gram of the product as a white solid (80%). NMR complies with structure. Elemental analysis: 57.05%; C, 7.18%; N, 6.16%; H (Theory for 1:1 salt: 56.99%; C, 7.39%; N, 6.11%; H)

Example 4b

Characterisation of the Alpha Form of the Hydrobromide of Compound I

The alpha form of the hydrobromide, as prepared in example 4a, is crystalline (XRPD)—see FIG. 2. It has a melting point of ~226° C. It absorbs about 0.3% of water when exposed to high relative humidity and has a solubility of 2 mg/ml in water.

Example 4c

Preparation of the Beta Form of the Hydrobromide Salt of Compound I 49.5 gram of 1-[2-(2,4-Dimethylphenylsulfanyl)-phenyl]piperazine colourless oil was dissolved in 500 ml ethyl acetate and added 18.5 ml 48%-wt HBr (aq). This addition caused formation of a thick slurry which was stirred over night at room temperature. Filtration and drying in vacuum (50° C.) over night produced the product in 29.6 gram as white solid (47%).

NMR complies with structure. Elemental analysis: 56.86%; C, 7.35%; N, 6.24%; H
(Theory for 1:1 salt: 56.99%; C, 7.39%; N, 6.11%; H)

Example 4d

Characterisation of the Beta Form of the Hydrobromide of Compound I

The beta form of the hydrobromide, as prepared in example 4c, is crystalline (XRPD) see FIG. 3. It has a melting point of ~231° C. It absorbs about 0.6% of water when exposed to high relative humidity and has a solubility of 1.2 mg/ml in water.

Example 4e

Preparation of the Gamma Form of the Hydrobromide Salt of Compound I 1 g of 1-[2-(2,4-Dimethylphenylsulfanyl)-phenyl]piperazine hydrobromide as prepared in example 4a was added 20 ml water and heated to 85° C. The solution was almost clear. Addition of 1 drop of HBr made it clear. HBr was added until cloud point was observed. The solution was cooled to room temperature and dried. NMR complies with structure. Elemental analysis: 56.63%; C, 7.18%; N, 6.21%; H (Theory for 1:1 salt: 56.99%; C, 7.39%; N, 6.11%; H)

Example 4f

Characterisation of the Gamma Form of the Hydrobromide of Compound I

Figure 4:
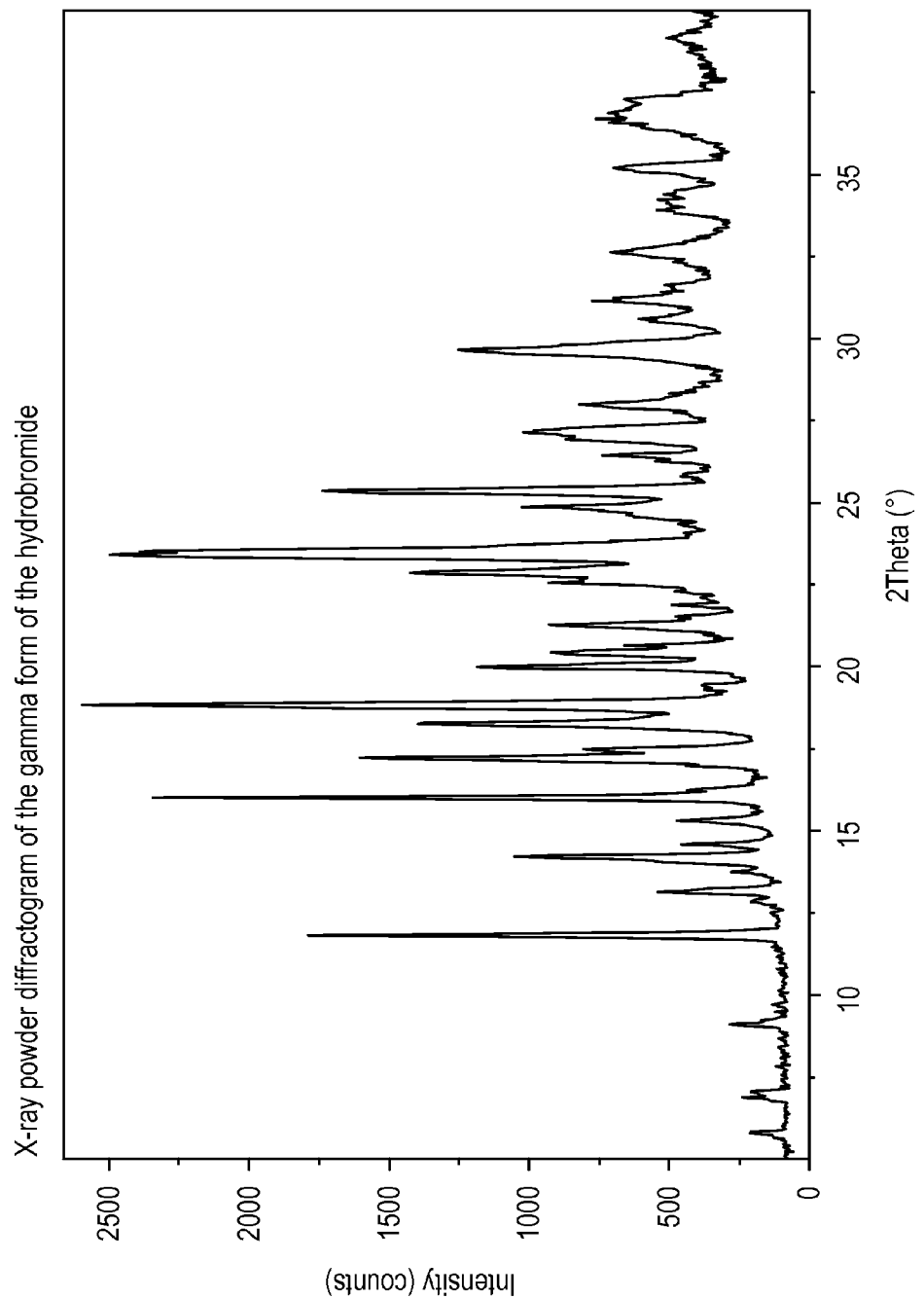

The hydrobromide, as prepared in example 6e, is crystalline (XRPD)—see FIG. 4. The DSC curve shows some thermal events at about 100° C.; probably change in crystal form. Then it melts at about 220° C. It absorbs about 4.5% of water when exposed to high relative humidity and at 30% RH at room temperature about 2% of water is absorbed.

Example 4g

Preparation of the Hydrobromide Hydrate of Compound I 1.4 gram of 1-[2-(2,4-Dimethylphenylsulfanyl)-phenyl]piperazine oil was added 20 ml water, and heated to 60° C. pH was adjusted to 1 using 48% HBr. The solution was cooled to room temperature and dried. NMR complies with structure. Elemental analysis: 55.21%; C, 7.16%; N, 6.34%; H (Theory for 1:1 salt hemihydrate: 55.68%; C, 7.21%; N, 6.23%; H)

Example 4h

Characterisation of the Hemi Hydrate of the Hydrobromide of Compound I

Figure 5:
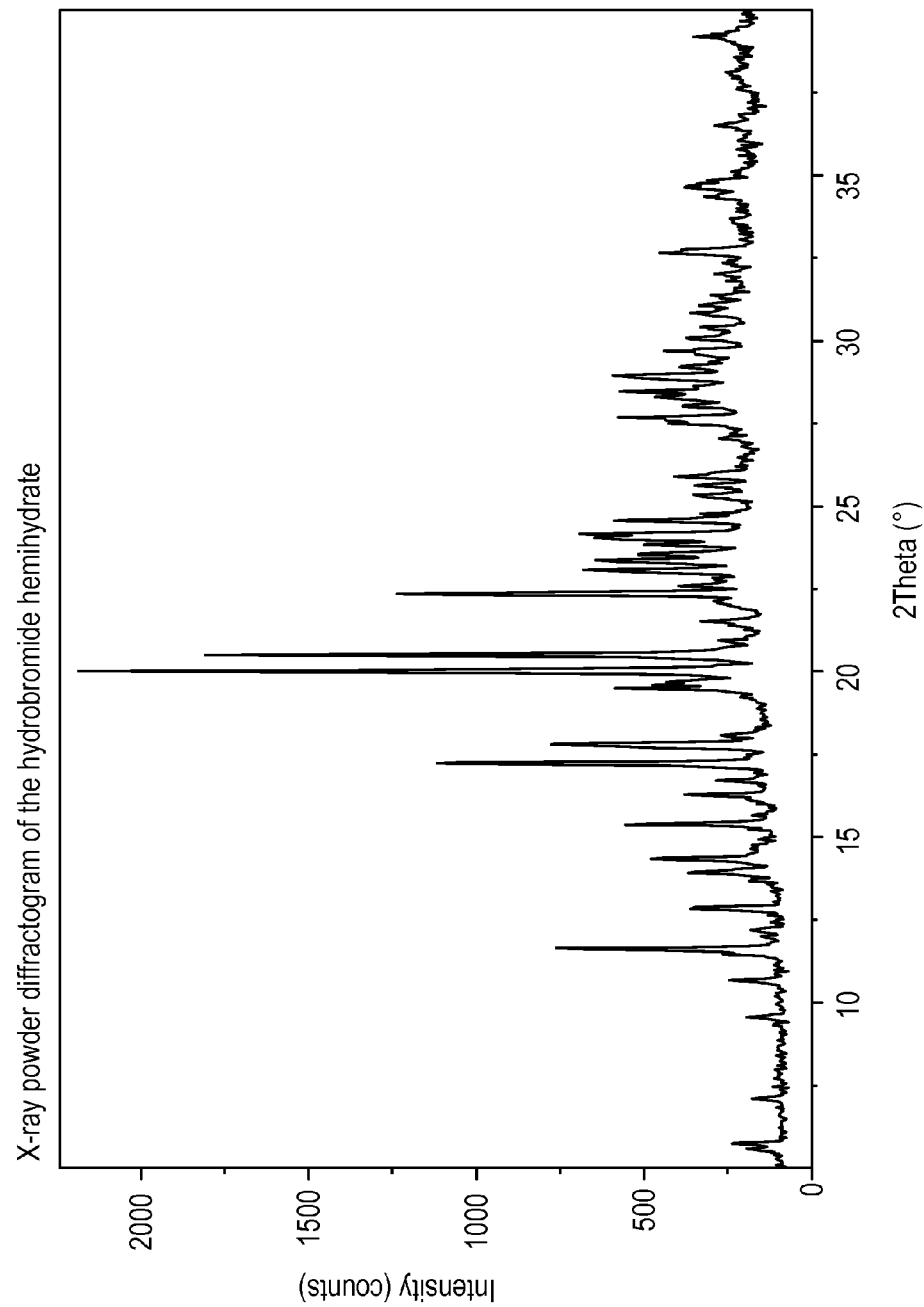

The hydrate as prepared in Example 4g is crystalline (XRPD)—see FIG. 5.
The water content depends strongly on the relative humidity. At room temperature and 95% RH the water content is about 3.7%. Dehydration occurs by heating to about 100° C.

Example 4i

Preparation of the Ethyl Acetate Solvate of the Hydrobromide Salt of Compound I 0.9 gram of 1-[2-(2,4-Dimethylphenylsulfanyl)-phenyl]piperazine oil was dissolved in 35 ml ethyl acetate and added 0.5 ml 48%-wt HBr (aq). This addition caused formation of a thick slurry which was stirred over night at room temperature. Filtration and washing with 30 ml diethyl ether followed by drying in vacuum (50° C.) over night produced 1-[2-(2,4-Dimethylphenylsulfanyl)-phenyl]piperazine HBr EtOAc solvate in 1.0 gram (65%). NMR complies with structure. Elemental analysis: 56.19%; C, 6.60%; N, 6.56%; H (Theory for 1:1 salt when corrected for 8% of Ethyl acetate and 0.5% water as determined by TGA and KF: 56.51%; C, 6.76%; N, 6.38%; H).

Example 4j

Characterisation of the Ethyl Acetate Solvate of the Hydrobromide of Compound I

Figure 6:
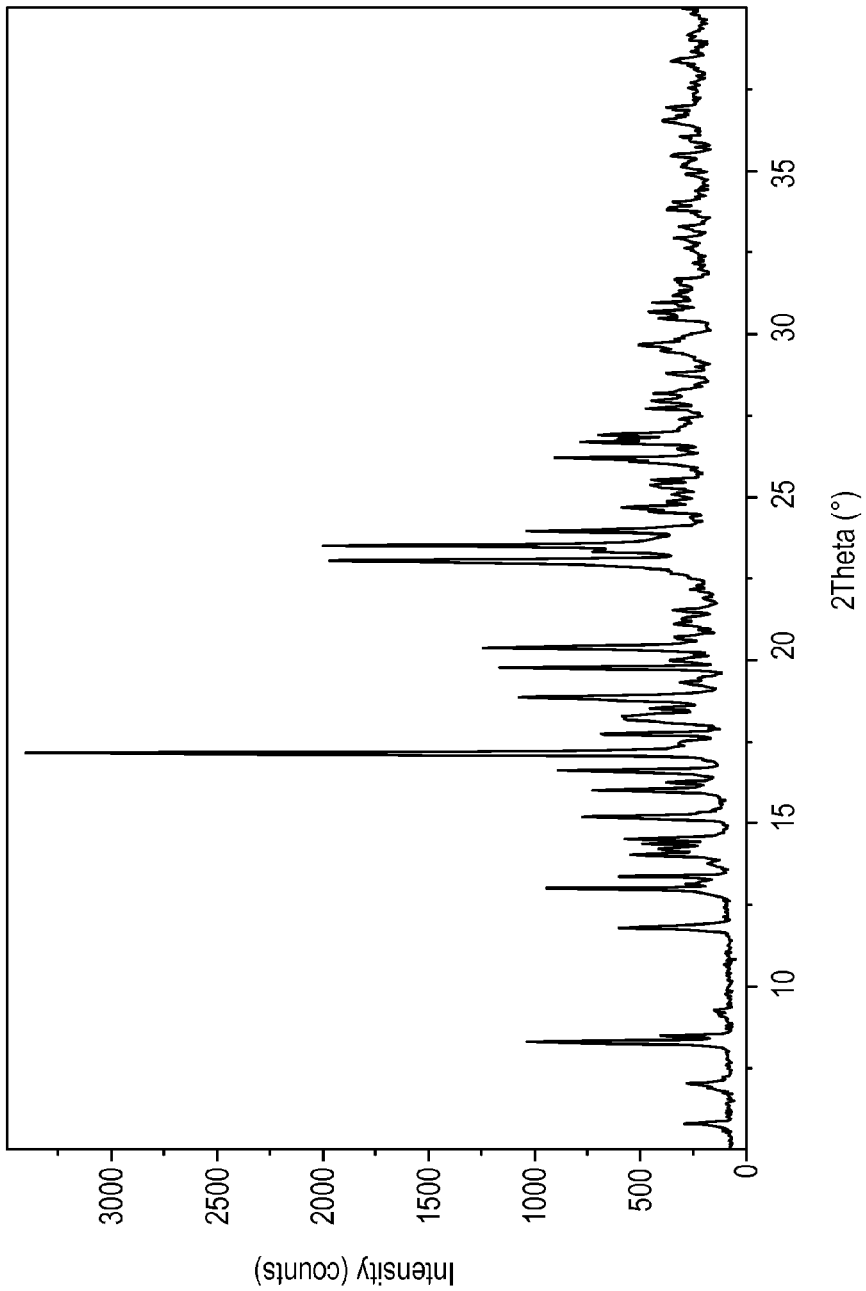

The ethyl acetate solvate, as prepared in example 4i, is crystalline (XRPD)—see FIG. 6. The batch contains a mixture of the solvate and the alpha form of compound I, probably because the drying has caused partly desolvation. The desolvation starts at ~75° C. when heated 10°/min. After desolvation the alpha form is formed.

If exposed to high relative humidity, the ethyl acetate is replaced by water, which is released when the humidity subsequently is lowered. The resulting solid is hygroscopic and absorbs 3.2% of water at high relative humidity.

Example 5a

Preparation of Hydrochloride Salt of Compound I 1.0 gram of 1-[2-(2,4-Dimethylphenylsulfanyl)-phenyl]piperazine oil was dissolved in 20 ml ethyl acetate using gentle heating (30° C.). When a clear solution was obtained a solution of 2 M HCl in diethyl ether was added slowly until pH was approximately 1-2. During the addition spontaneous precipitation was observed. After final addition the suspension was stirred for 1 hour before the white precipitate was isolated by filtration and dried in vacuum (40° C.) overnight. 1-[2-(2,4-Dimethylphenylsulfanyl)-phenyl]piperazine hydrochloride was isolated in 1.1 gram (99%).

NMR complies with structure. Elemental analysis: 64.18%; C, 8.25%; N, 6.96%; H (Theory for 1:1 salt when corrected for 0.66% of water as determined by TGA: 64.13%; C, 8.31%; N, 6.95%; H)

Example 5b

Characterisation of the Hydrochloride of Compound I

Figure 7:
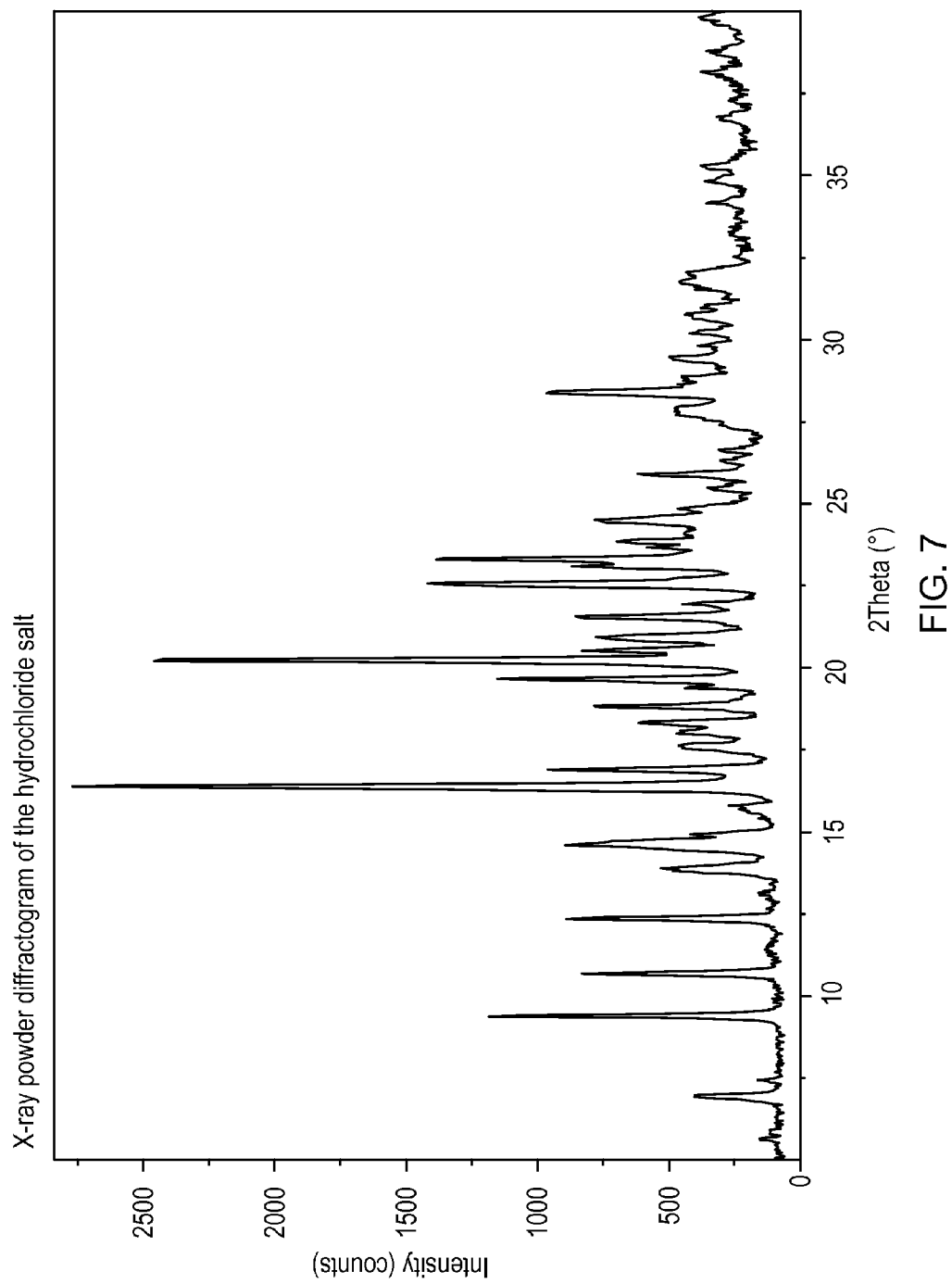

The hydrochloride, as prepared in example 5a, is crystalline (XRPD)—see FIG. 7. It has a melting point of ~236° C. It absorbs about 1.5% of water when exposed to high relative humidity and has a solubility of 3 mg/ml in water.

Example 5c

Preparation of the Hydrochloride Monohydrate of Compound I 11.9 gram of 1-[2-(2,4-Dimethylphenylsulfanyl)-phenyl]piperazine oil was dissolved in 100 ml ethanol using heating. When a homogenous solution was obtained addition of 3.5 ml conc. HCl(aq) took place causing the immediately precipitation of a white solid. The suspension was stirred for 5 minutes at first and then on ice-bath another hour before filtration. The white solid was washed using 100 ml of fresh cool ethanol (placed in freezer at −18° C. for 2 hours), 50 ml acetone and finally 50 ml diethyl ether before dried in vacuum (50° C.) overnight. 1-[2-(2,4-Dimethylphenylsulfanyl)-phenyl]piperazine HCl was isolated in 5.1 gram (38%).

NMR complies with structure. Elemental analysis: 61.23%; C, 7.91%; N, 7.16%; H (Theory for 1:1 salt monohydrate: 61.26%; C, 7.94%; N, 7.14%; H)

Example 5d

Characterisation of the Hydrochloride Monohydrate of Compound I

Figure 8:
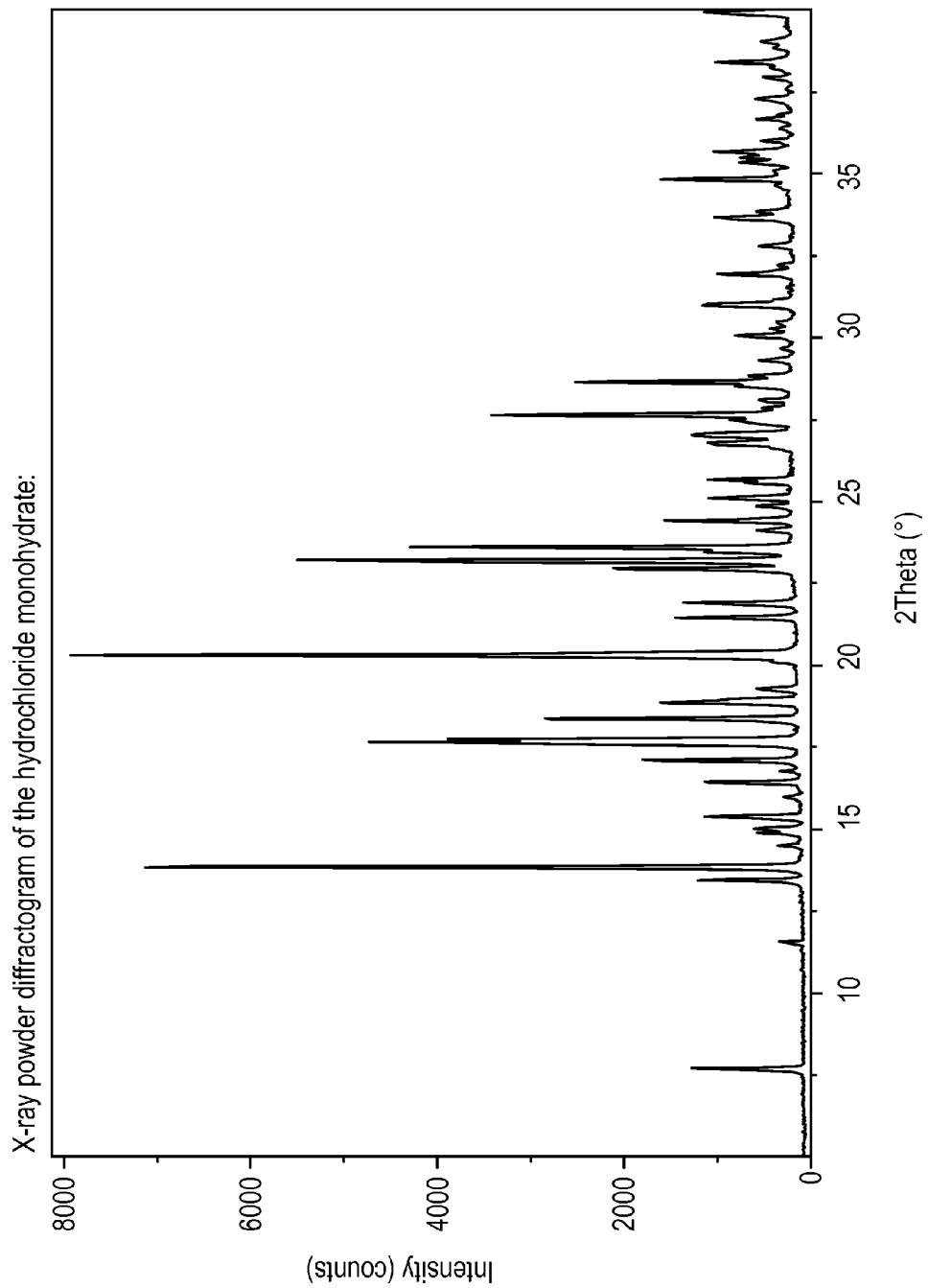

The hydrochloride monohydrate, as prepared in example 5c, is crystalline (XRPD)—see FIG. 8. It dehydrates starting at about 50° C. Some thermal events, probably rearrangement, occur by further heating, and it melts at about 230° C. followed by recrystallisation and melting at about 236° C. It does not absorb further amount of water when exposed to high relative humidity and the hydrate bounded water is not released until the relative humidity is decreased to below 10% RH at room temperature. It has a solubility of about 2 mg/ml in water.

Example 6a

Preparation of Mesylate Salt of Compound I 1.0 gram of 1-[2-(2,4-Dimethylphenylsulfanyl)-phenyl]piperazine oil was dissolved in 20 ml ethyl acetate by heating (70° C.). When a clear solution was obtained 0.35 gram of methane sulphonic acid (1.1 eqv.) was added slowly. After final addition the solution was cooled on ice and diethyl ether was added slowly causing the precipitation of the product. The suspension was stirred for 2 hours on ice before the white precipitate was isolated by filtration and dried in vacuum (40° C.) overnight. 1-[2-(2,4-Dimethylphenylsulfanyl)-phenyl]piperazine mesylate was isolated in 1.1 gram (85%). NMR complies with structure. Elemental analysis: 57.81%; C, 6.81%; N, 6.68%; H (Theory for a 1:1 salt: 57.81%; C, 7.10%; N, 6.64%; H)

Example 6b

Characterisation of the Mesylate of Compound I

Figure 9:
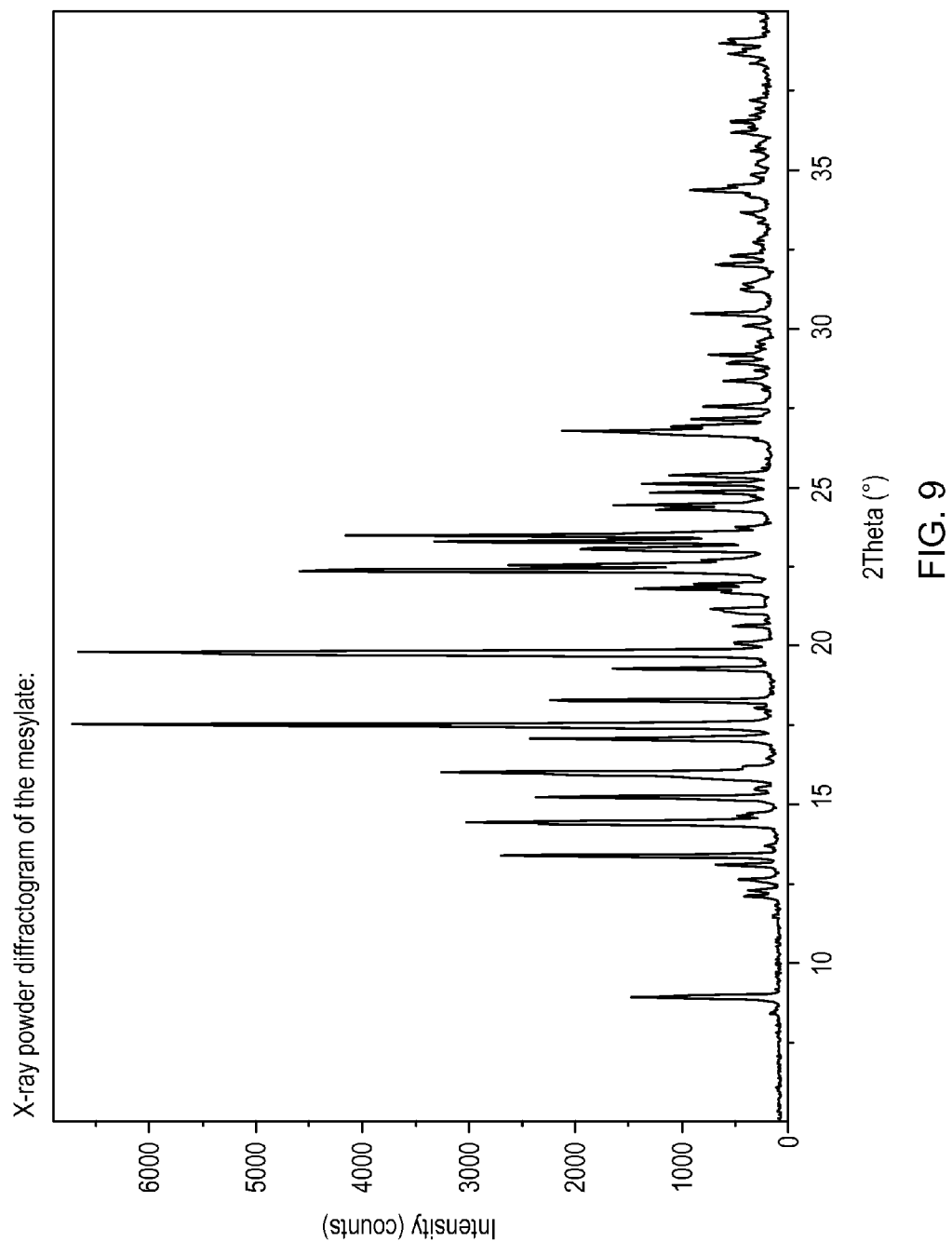

The mesylate, as prepared in example 7a, is crystalline (XRPD)—see FIG. 9. It has a melting point of ~163° C. It is hygroscopic (absorbs about 8% of water when exposed to 80% relative humidity and is thereby transformed into a hydrated form. The last 6% of the absorbed water is not released until the relative humidity is below 10% RH. It has a very high solubility in water (>45 mg/ml).

Example 7a

Preparation of Fumarate of Compound I 5.5 gram 1-[2-(2,4-Dimethylphenylsulfanyl)-phenyl]piperazine oil was heated to reflux in a mixture of 50 ml methanol and 50 ml ethyl acetate. The solution was left to cool slightly before addition of 2.1 gram fumaric acid took place causing an exothermic reaction and precipitation of a white solid. The suspension was stirred while being allowed to cool to room temperature followed by 2 hours in the freezer at −18° C. The white solid was collected by filtration and washed with 20 ml cold ethyl acetate before drying in vacuum (50° C.) over night. The product was isolated in 3.1 gram (44%).

NMR complies with structure. Elemental analysis: 63.42%; C, 6.64%; N, 6.42%; H (Theory for a 1:1 salt: 63.74%; C, 6.76%; N, 6.32%; H)

Example 7b

Characterisation of the Fumarate of Compound I

Figure 10:
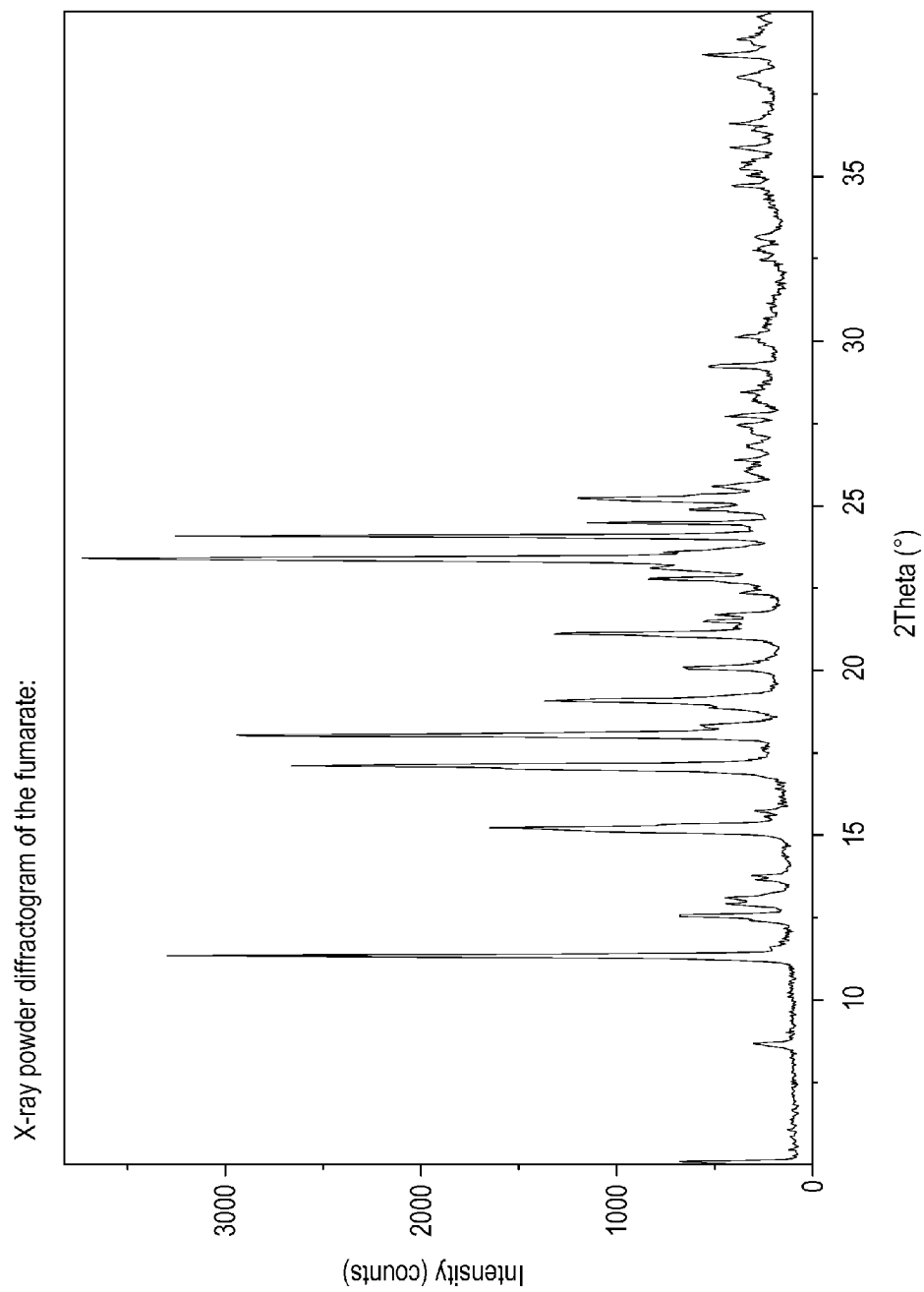

The fumarate, as prepared in example 7a, is crystalline (XRPD)—see FIG. 10. It has a melting point of ~194° C. The solubility in water is 0.4 mg/ml.

Example 8a

Preparation of Maleate of Compound I 2.5 gram 1-[2-(2,4-Dimethylphenylsulfanyl)-phenyl]piperazine oil was dissolved in 50 ml ethyl acetate and heated to 60° C. followed by addition of 1.1 gram maleic acid. The mixture was heated again to reflux for 5 minutes and left to cool to room temperature while stirring. During the cooling precipitation started and was finalized by 4 hours in the freezer (−18° C.). The white solid was collected by filtration and washed with 50 ml diethyl ether before drying in vacuum (50° C.) over night. This produced 1.3 gram of 1-[2-(2,4-Dimethylphenylsulfanyl)-phenyl]piperazine Maleate (38%) that was recrystallised by treatment with 40 ml ethyl acetate and 5 ml methanol at reflux. The clear solution was cooled to room temperature followed by 2 hours in the freezer (−18° C.) before filtering and washed twice with 10 ml cold ethyl acetate followed by drying in vacuum (50° C.) for two days. 1-[2-(2,4-Dimethylphenylsulfanyl)-phenyl]piperazine Maleate was isolated in 0.9 gram (69%). NMR complies with structure. Elemental analysis: 63.57%; C, 6.79%; N, 6.39%; H (Theory for a 1:1 salt: 63.74%; C, 6.76%; N, 6.32%; H)

Example 8b

Characterisation of the Maleate of Compound I

Figure 11:
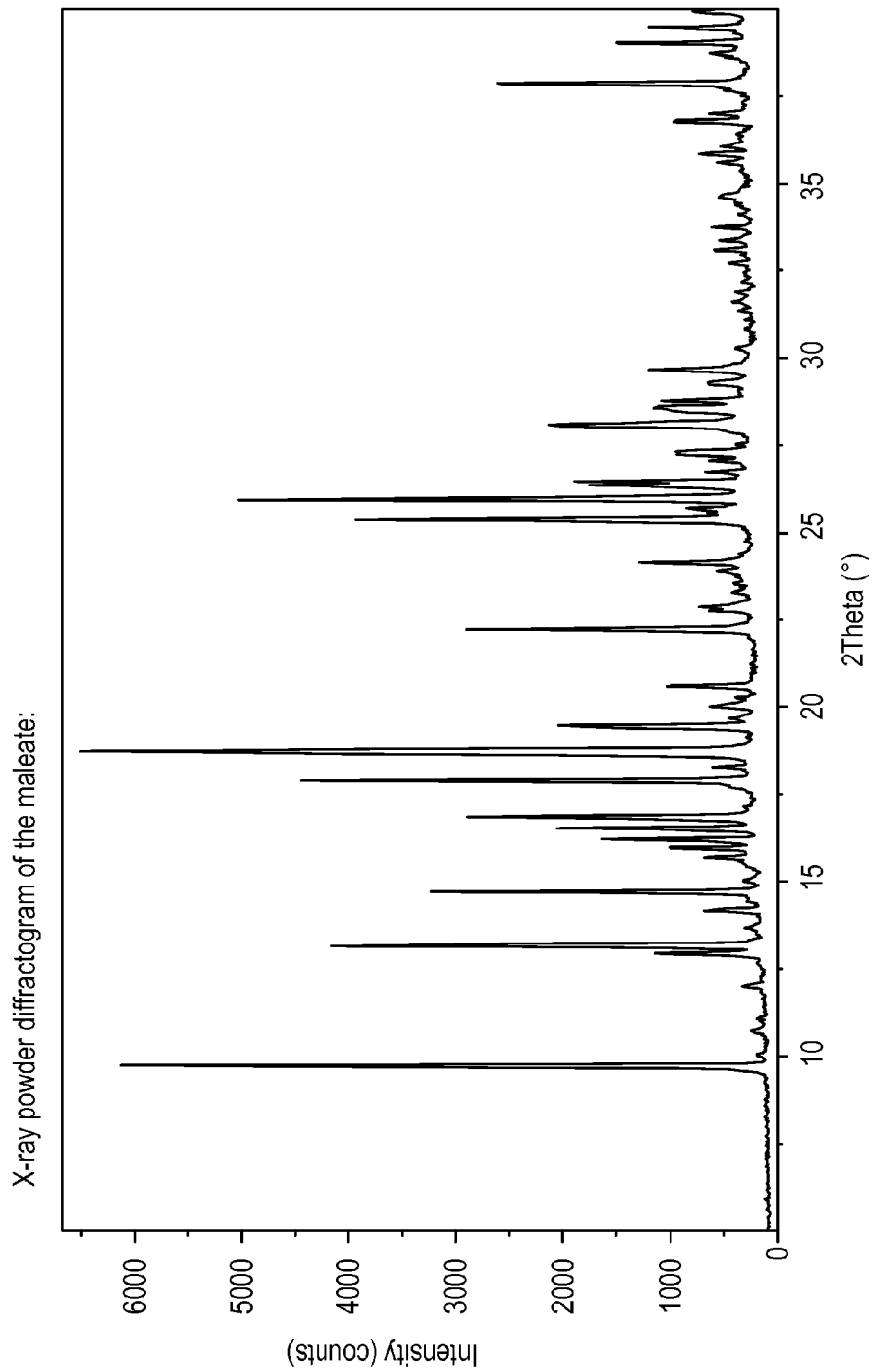

The maleate, as prepared in example 8a, is crystalline (XRPD)—see FIG. 11. It has a melting point of ~152° C. The solubility in water is ~1 mg/ml.

Example 9a

Preparation of Meso-Tartrate of Compound I 11.1 ml of a 0.30 M solution of 1-[2-(2,4-Dimethylphenylsulfanyl)-phenyl]piperazine in acetone was treated with 0.5 gram meso-tartaric acid dissolved in 5 ml acetone. The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine meso-tartaric acid was isolated in 1.4 gram (93%). NMR complies with structure. Elemental analysis: 58.58%; C, 6.29%; N, 6.40%; H (Theory for a 1:1 salt: 58.91%; C, 6.25%; N, 6.29%; H)

Example 9b

Characterisation of the Meso-Tartrate of Compound I

Figure 12:
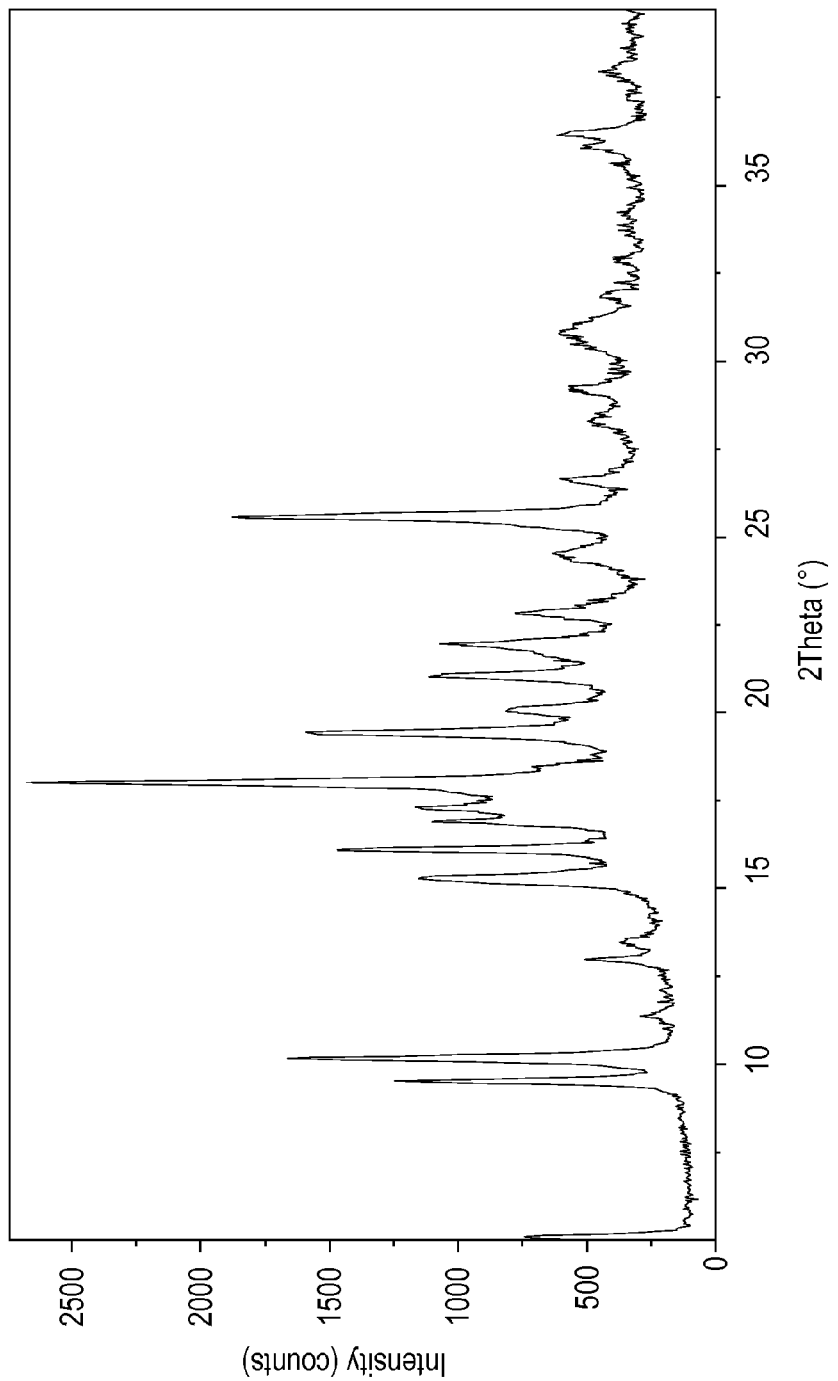

The meso-tartrate, as prepared in example 9a, is crystalline (XRPD)—see FIG. 12. It has a melting point of ~164° C. The solubility in water is ~0.7 mg/ml.

Example 10a

Preparation of L-(+)-Tartrate of Compound I 11.1 ml of a 0.30 M solution of 1-[2-(2,4-Dimethylphenylsulfanyl)-phenyl]piperazine in acetone was treated with 0.5 gram L-(+)-tartaric acid dissolved in 5 ml acetone. The mixture was stirred at room temperature for 30 minutes during which precipitation took place. Filtration and washing first with 5 ml acetone and then 3 ml diethyl ether achieved the product as a white solid that was dried in vacuum (50° C.) over night. 1-[2-(2,4-Dimethylphenylsulfanyl)-phenyl]piperazine (+)-tartaric acid was isolated in 1.2 gram (81%). NMR complies with structure. Elemental analysis: 58.86%; C, 6.30%; N, 6.38%; H (Theory for a 1:1 salt: 58.91%; C, 6.25%; N, 6.29%; H)

Example 10b

Characterisation of the L-(+)-Tartrate of Compound I

Figure 13:
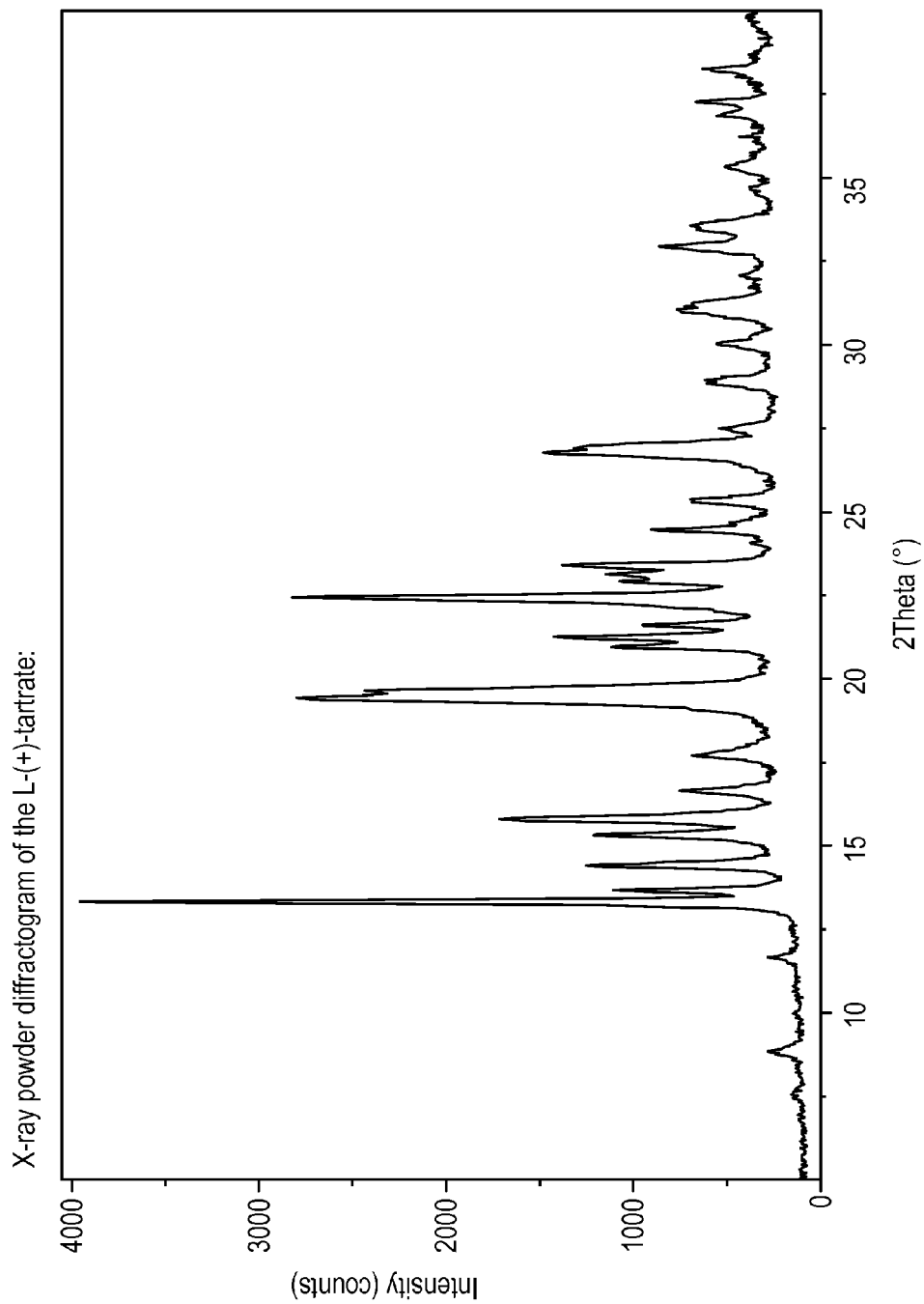

The L-(+)-tartrate, as prepared in example 10a, is crystalline (XRPD)—see FIG. 13. It has a melting point of ~171° C. The solubility in water is ~0.4 mg/ml.

Example 11a

Preparation of D-(−)-Tartrate of Compound I 11.1 ml of a 0.30 M solution of 1-[2-(2,4-Dimethylphenylsulfanyl)-phenyl]piperazine in acetone was treated with 0.5 gram D-(−)-tartaric acid dissolved in 5 ml acetone. The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine D-(−)-tartaric acid was isolated in 1.0 gram (68%). NMR complies with structure. Elemental analysis: 58.90%; C, 6.26%; N, 6.35%; H (Theory for a 1:1 salt: 58.91%; C, 6.25%; N, 6.29%; H)

Example 11b

Characterisation of the D-(−)-Tartrate of Compound I

Figure 14:
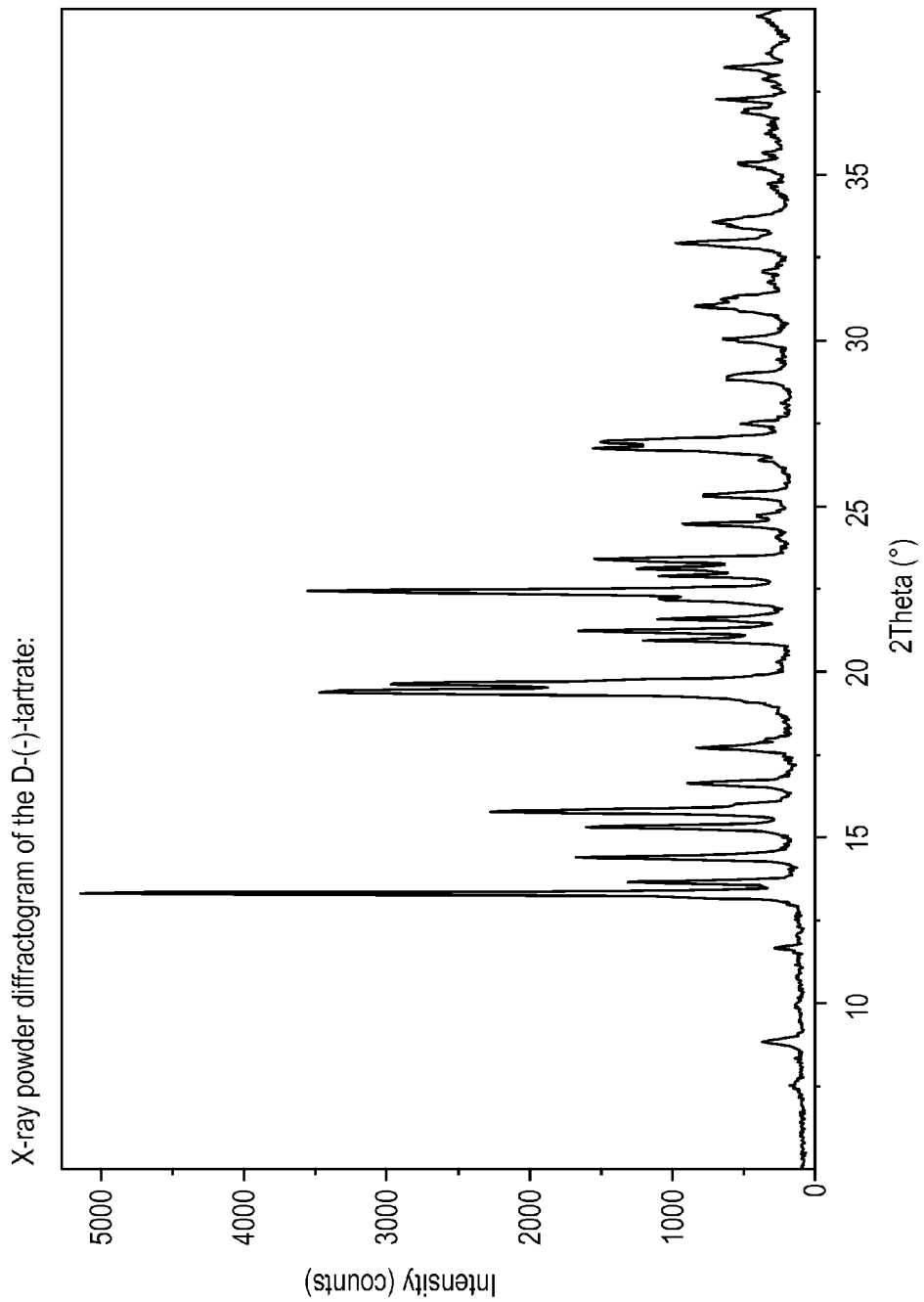

The D-(+)-tartrate, as prepared in example 11a, is crystalline (XRPD)—see FIG. 14. It has a melting point of ~175° C. The solubility in water is ~0.4 mg/ml.

Example 12a

Preparation of Sulphate of Compound I 11.1 ml of a 0.30 M solution of 1-[2-(2,4-Dimethylphenylsulfanyl)-phenyl]piperazine in acetone was treated with 2.2 ml of a 3 M solution of $H_2SO_4$ (aq). The mixture was stirred at room temperature for 30 minutes and then on ice-bath for another 4 hours before precipitation took place and was finalized. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine sulphate was isolated in 0.51 gram (39%). NMR complies with structure. Elemental analysis: 54.53%; C, 7.22%; N, 6.28%; H (Theory for a 1:1 salt: 54.52%; C, 7.07%; N, 6.10%; H)

Example 12b

Characterisation of the Sulphate of Compound I

Figure 15:
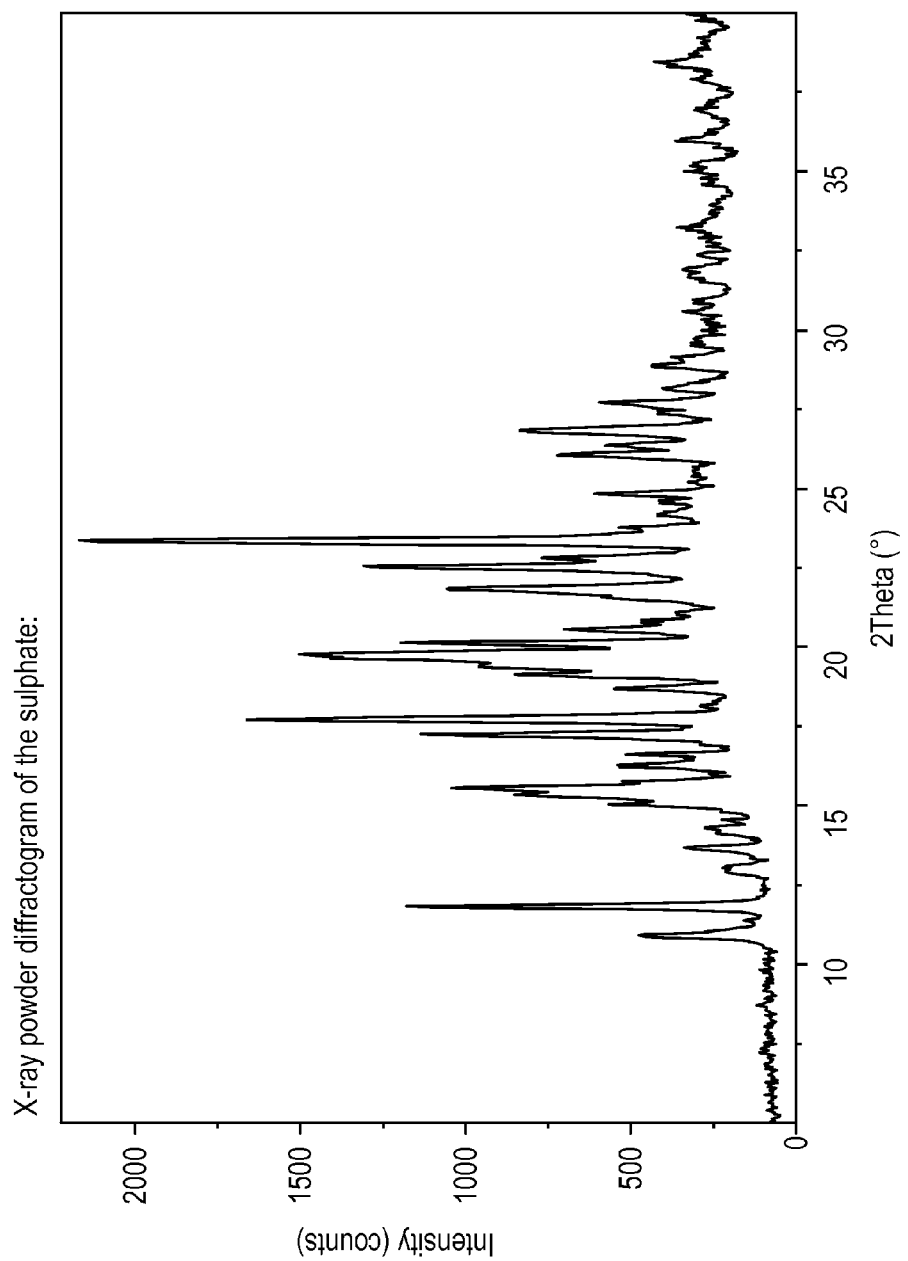

The sulphate, as prepared in example 12a, is crystalline (XRPD)—see FIG. 15. It has a melting point of ~166° C. The solubility in water is ~0.1 mg/ml.

Example 13a

Preparation of Phosphate of Compound I 11.1 ml of a 0.30 M solution of 1-[2-(2,4-Dimethylphenyl-sulfanyl)-phenyl]piperazine in acetone was treated with 0.2 ml 65% $H_3PO_4$ (aq). The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine phosphate was isolated in 1.23 gram (94%). NMR complies with structure. Elemental analysis: 54.21%; C, 7.15%; N, 6.43%; H (Theory for a 1:1 salt: 54.53%; C, 7.07%; N, 6.36%; H)

Example 13b

Characterisation of the Phosphate of Compound I

Figure 16:
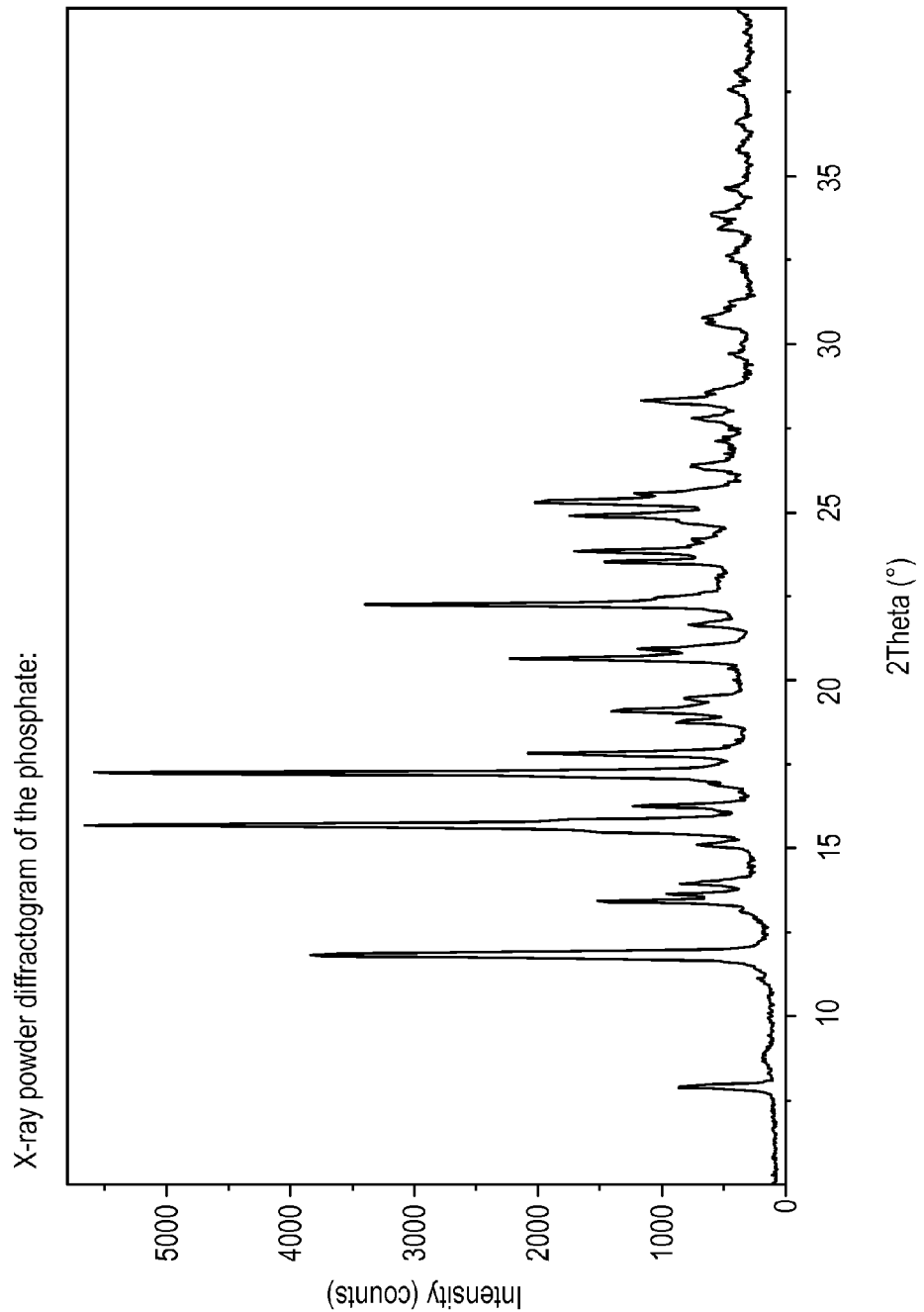

The phosphate, as prepared in example 13a, is crystalline (XRPD) see FIG. 16. It has a melting point of ~224° C. The solubility in water is ~1 mg/ml.

Example 14a

Preparation of Nitrate of Compound I 11.1 ml of a 0.30 M solution of 1-[2-(2,4-Dimethylphenyl-sulfanyl)-phenyl]piperazine in acetone was treated with 0.2 ml of 16.5 M $HNO_3$ (aq). The mixture was stirred at room temperature for 30 minutes during which precipitation took place. Filtration and washing first with 5 ml acetone and then 3 ml diethyl ether produced the product as a white solid that was dried in vacuum (50° C.) over night. 1-[2-(2,4-Dimethylphenylsulfanyl)-phenyl]piperazine nitrate was isolated in 0.87 gram (73%). NMR complies with structure. Elemental analysis: 59.80%; C, 11.67%; N, 6.51%; H (Theory for a 1:1 salt: 59.81%; C, 11.63%; N, 6.41%; H)

Example 14b

Characterisation of the Nitrate of Compound I

Figure 17:
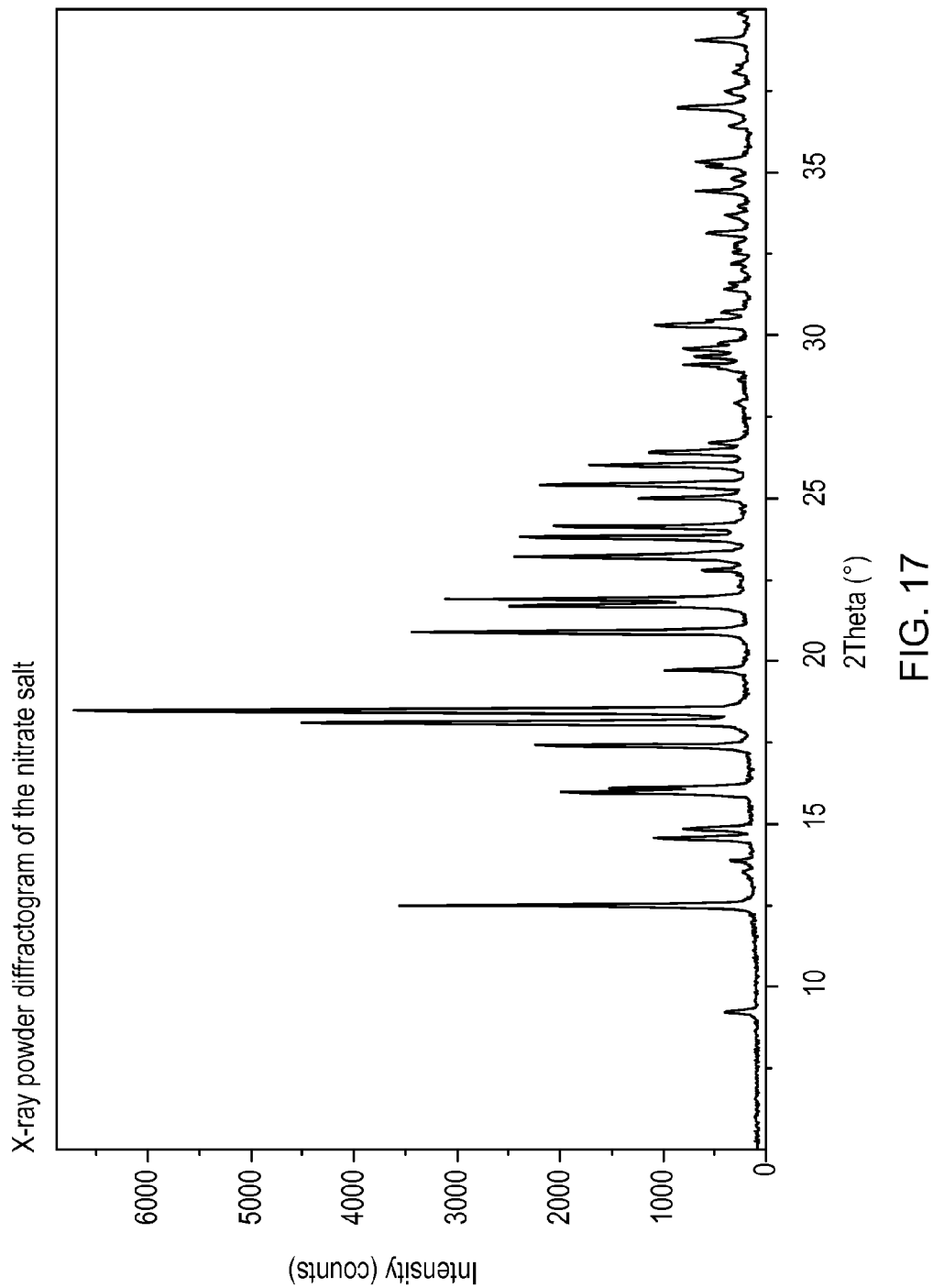

The nitrate, as prepared in example 14a, is crystalline (XRPD)—see FIG. 17. It does not melt but decomposes under an exothermic reaction at about 160° C. The solubility in water is ~0.8 mg/ml.

Example 15

Tablet

The examples below show representative examples of how tablets comprising compounds of the present invention may be prepared. The beta form of the hydromide salt has been used in all examples.

Example 15a 63.55 g of the hydrobromide salt, 923.65 g Lactosum 350M, 461.8 g corn starch and 76.0 g Kollidon VA64 were mixed for 2 minutes in a Diosna PP1 high shear mixer at an impeller speed of 1000 rpm. Next, the speed of the impeller was lowered to 800 rpm and 220 g water was added during the course of a minute. Massing was performed for 7 minutes and the resulting granules were passed through a sieve, size 4000 μm. The granules were dried and passed through a sieve, size 710 μm. 1383.5 g of the resulting granules were mixed with 400 g Avicel PH200 and 60 g Ac-Di-Sol. Following lubrication of the blend by mixing with 15 g magnesium stearate the powder blend was transferred to a tablet press. Tablets having a target core weight of 200 mg and a diameter of 8 mm were prepared to obtain tablets with a target content corresponding to 5 mg of the free base.

Example 15b 317.75 g of the hydrobromide salt, 754.15 g Lactosum 350M, 377.1 g corn starch and 76.0 g Kollidon VA64 were mixed for 2 minutes in a Diosna PP1 high shear mixer at an impeller speed of 1000 rpm. Next, the speed of the impeller was lowered to 800 rpm and 210 g water was added during the course of a minute. Massing was performed for 7 minutes and the resulting granules were passed through a sieve, size 4000 μm. The granules were dried and passed through a sieve, size 710 μm. 1386.2 g of the resulting granules were mixed with 400 g Avicel PH200 and 60 g Ac-Di-Sol. Following lubrication of the blend by mixing with 15 g magnesium stearate the powder blend was transferred to a tablet press. Tablets having a target core weight of 200 mg and a diameter of 8 mm were prepared to obtain tablets with a target content corresponding to 25 mg of the free base.

Example 15c 32.2 g of the hydrobromide salt, 944.82 g Lactosum 350M, 472.4 g corn starch and 76.0 g Kollidon VA64 were mixed for 2 minutes in a Diosna PP1 high shear mixer at an impeller speed of 1000 rpm. Next, the speed of the impeller was lowered to 800 rpm and 220 g water was added during the course of a minute. Massing was performed for 7 minutes and the resulting granules were passed through a sieve, size 4000 μm. The granules were dried and passed through a sieve, size 710 μm. 1317 g of the resulting granules were mixed with 400 g Avicel PH200 and 60 g Ac-Di-Sol. Following lubrication of the blend by mixing with 15 g magnesium stearate the powder blend was transferred to a tablet press. Tablets having a target core weight of 208 mg and a diameter of 8 mm were prepared to obtain tablets with a target content corresponding to 2.5 mg of the free base.

Example 15d 540.85 g of the hydrobromide salt, 953.00 g Pearlitol 50C, 296.22 g corn starch and 70.5 g Kollidon VA64 were mixed for 2 minutes in an Aeromatic-Fielder PMA1 high shear mixer at an impeller speed of 1000 rpm. Next, the speed of the impeller was lowered to 800 rpm and 241.87 g water was added during the course of a minute. Massing was performed for 7 minutes and the resulting granules were passed through a sieve, size 4000 μm. The granules were dried and passed through a sieve, size 710 μm. 1500 g of the resulting granules were mixed with 531.91 g Avicel PH200 and 85.11 g Primojel. Following lubrication of the blend by mixing with 10.64 g magnesium stearate the powder blend was transferred to a tablet press. Tablets having a target core weight of 125 mg and a diameter of 6 mm were prepared to obtain tablets with a target content corresponding to 25 mg of the free base.

Example 15e 270.45 g of the hydrobromide salt, 772.0 g Pearlitol 50C, 386.41 g corn starch and 70.5 g Kollidon VA64 were mixed for 2 minutes in an Aeromatic-Fielder PMA1 high shear mixer at an impeller speed of 1000 rpm. Next, the speed of the impeller was lowered to 800 rpm and 195 g water was added during the course of a minute. Massing was performed for 5.5 minutes and the resulting granules were passed through a sieve, size 4000 µm. The granules were dried and passed through a sieve, size 710 µm. 1200.3 g of the resulting granules were mixed with 425.5 g Avicel PH200 and 68.09 g Primojel. Following lubrication of the blend by mixing with 8.8 g magnesium stearate the powder blend was transferred to a tablet press. Tablets having a target core weight of 100 and a diameter of 6 mm were prepared to obtain tablets with a target content corresponding to 10 mg of the free base.

Example 15f 504.85 g of the free base, 552.95 g Pearlitol 50C, 276.53 g corn starch and 65.7 g Kollidon VA64 were mixed for 2 minutes in an Aeromatic-Fielder PMA1 high shear mixer at an impeller speed of 1000 rpm. Next, the speed of the impeller was lowered to 800 rpm and 182 g water was added during the course of a minute. Massing was performed for 5.5 minutes and the resulting granules were passed through a sieve, size 4000 µm. The granules were dried and passed through a sieve, size 710 µm. 1250.7 g of the resulting granules were mixed with 443.31 g Avicel PH200 and 70.8 g Primojel. Following lubrication of the blend by mixing with 8.92 g magnesium stearate the powder blend was transferred to a tablet press. Tablets having a target core weight of 250 mg and a diameter of 8 mm were prepared to obtain tablets with a target content corresponding to 50 mg of the free base.

Example 15g 135.23 g of the hydrobromide salt, 863.2 g Pearlitol 50C, 432.69 g corn starch and 70.66 g Kollidon VA64 were mixed for 2 minutes in an Aeromatic-Fielder PMA1 high shear mixer at an impeller speed of 1000 rpm. Next, the speed of the impeller was lowered to 800 rpm and 195 g water was added during the course of a minute. Massing was performed for 5.5 minutes and the resulting granules were passed through a sieve, size 4000 µm. The granules were dried and passed through a sieve, size 710 µm. 1200 g of the resulting granules were mixed with 425.28 g Avicel PH200 and 68.2 g Primojel. Following lubrication of the blend by mixing with 8.58 g magnesium stearate the powder blend was transferred to a tablet press. Tablets having a target core weight of 100 mg and a diameter of 6 mm were prepared to obtain tablets with a target content of corresponding to 5 mg of the free base.

Example 15h 67.6 g of the hydrobromide salt, 908.0 g Pearlitol 50C, 453.9 g corn starch and 70.51 g Kollidon VA64 were mixed for 2 minutes in an Diosna PP1 high shear mixer at an impeller speed of 1000 rpm. Next, the speed of the impeller was lowered to 800 rpm and 195 g water was added during the course of a minute. Massing was performed for 5.5 minutes and the resulting granules were passed through a sieve, size 4000 µm. The granules were dried and passed through a sieve, size 710 µm. 1325 g of the resulting granules were mixed with 531.91 g Avicel PH200 and 85.11 g Primojel. Following lubrication of the blend by mixing with 10.64 g magnesium stearate the powder blend was transferred to a tablet press. Tablets having a target core weight of 207.8 mg and a diameter of 7 mm were prepared to obtain tablets with a target content corresponding to 5 mg of the free base.

Example 15i 2290.1 g of the hydrobromide salt, 17568 g anhydrous calcium hydrogen phosphate and 8783 g of corn stach and 1510 g copovidone were mixed for 3 minutes in an Aeromatic-Fielder PMA100 high-shear mixer at an impeller speed of 200 rpm. Next, 5130 g water was added during the course of 2 minutes at an impeller speed of 150 rpm. Massing was performed for 15 minutes and the resulting granules were passed through a cone mill operating at about 2700 rpm with a screen, size 9.525 mm. The granules were dried and passed through cone mill operating at about 1500 rpm with a screen, size 2.388 mm. 28747 g of the resulting granules were mixed with 11250 g microcrystalline cellulose, 1350 g sodium starch glycolate (type A) and 1800 g talc. Following lubrication of the blend by mixing with 450 g magnesium stearate the powder blend was transferred to a tablet press. Tablets having a target core weight of 125 mg and a diameter of 6 mm were prepared to obtain tablets with a target content of the hydrobromide salt corresponding to 5 mg of the free base. In addition, tablets having a target core weight of 250 mg and a diameter of 8 mm were prepared to obtain tablets with a target content of the hydrobromide salt corresponding to 10 mg of the free base.

Example 16

Pain Effects in the Mouse Intradermal Formalin Test

In this model, mice receive an injection of formalin (4.5%, 20 µl) into the left hind paw. The irritation caused by the formalin injection elicits a characteristic biphasic behavioural response, as quantified by the amount of time spent licking the injured paw. The first phase (~0-10 minutes) represents direct chemical irritation and nociception, whereas the second (~20-30 minutes) is thought to represent pain of neuropathic origin. The two phases are separated by a quiescent period in which behaviour returns to normal. The effectiveness of test compounds to reduce the painful stimuli is assessed by counting the amount of time spent licking the injured paw in the two phases.

Compounds of the present invention showed a significant reduction in second phase pain scores (FIG. 18b), indicating efficacy against pain of neuropathic origin. Furthermore, the compounds of the present invention showed a significant reduction in the first phase scores (FIG. 18a), indicating a more analgesic action at the highest dose. In summary, these results indicate that compounds of the present invention are likely to be effective in the treatment of pain disorders.

Example 17

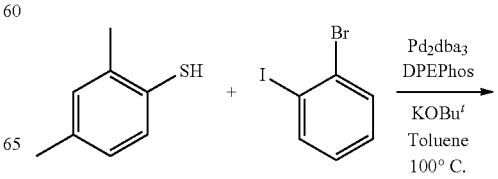

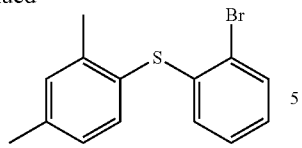

20 g 2-bromoiodobenzene (71 mmol) and 9.8 g 2,4-dimethylthiophenol (71 mmol) were dissolved in 100 ml toluene. The solution was purged with nitrogen before 324 mg Pd$_2$dba$_3$ (0.35 mmol; 1 mol-%) and 381 mg DPEPhos (0.71 mmol; 1 mol-%). The reaction mixture was stirred 5 min during which the colour changes from dark-red to orange. Addition of 8.7 g KOBu$^t$ (78 mmol) took place and a heterogeneous mixture was formed instantly. The suspension was heated to 100° C. under nitrogen. After 1 hour the mixture was cooled to 0° C. and stirred for 2 hours before filtering the mixture though a pad of celite. The filter cake was washed with 2×50 ml toluene and the combined filtrates evaporated to 21 g of a orange-reddish oil (99% yield) that proved >96% pure on HPLC and GC-MS.

Example 18

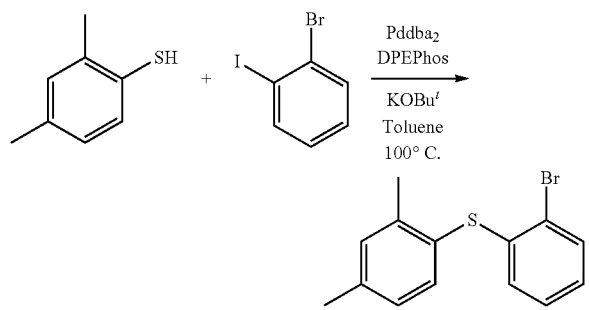

500 ml toluene was placed in a 1 L three necked round bottle with a mechanical stirrer and added 203 mg Pddba$_2$ (0.35 mmol; 0.1 mol-%) and 760 mg DPEPhos (1.5 mmol; 0.4 mol-%). The dark-red solution was purged with nitrogen for 5 minutes before addition of 100 g 2-bromoiodobenzene (353 mmol) and 48.9 g 2,4-dimethylthiophenol (353 mmol) took place. Addition of 43.6 g KOBu$^t$ (389 mmol) caused an exothermic reaction increasing the temperature from 20° C. to 36° C. simultaneously with the formation of heterogeneous mixture. The suspension was heated to 100° C. under nitrogen. After 7 hours the mixture was cooled to 0° C. and stirred for 2 hours before filtering the mixture though a pad of celite. The filter cake was washed with 2×200 ml toluene and the combined filtrates was evaporated to 104 g of an orange oil (105% yield) that proved 97% pure on HPLC and NMR conforms to desired structure. The oil solidified during standing at room temperature.

Example 19

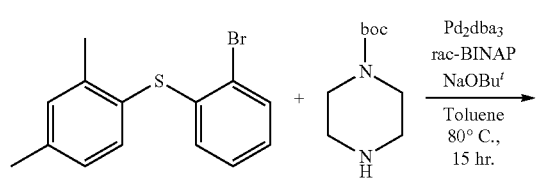

A solution of 10 gram 1-(2-Bromo-phenylsulfanyl)-2,4-dimethyl-benzene (34 mmol) in 50 ml dry toluene was added 7 gram boc-piperazine (38 mmol), degassed with nitrogen for 5 minutes, added 312 mg Pd$_2$dba$_3$ (2 mol-%) and 637 mg rac-BINAP (3 mol-%), degassed for another 5 minutes before adding 3.9 gram Bu$^t$ONa (41 mmol) and heated to 80° C. for 15 hours. The reaction mixture was cooled to RT and extracted twice with 20 ml 15% brine, dried over Na$_2$SO$_4$, added charcoal, refluxed for 15 minutes, filtered though celite and evaporated to 14.2 gram of brownish oil (4-[2-(2,4-Dimethyl-phenylsulfanyl)-phenyl]-BOC-piperazine) having a purity of 95% determined by NMR. The crude oil was dissolved in 200 ml MeOH and 20 ml 6M HCl (aq.) and refluxed for 1 hour after which HPLC showed full deprotection. After cooling to RT the methanol was removed by vacuum on a rotary-evaporator, 20 ml conc. NaOH (pH was measured to 13-14) was added after which the mixture was stirred 15 minutes with 100 ml EtOAc. The organic phase was collected and extracted twice with 30 ml 15% brine, dried over Na$_2$SO$_4$ and added 5.2 g fumaric acid (44 mmol) in 30 ml MeOH. During heating to reflux a homogenous solution forms from which a rapid precipitation takes place either during further heating or upon cooling. The precipitate was collected, washed with 20 ml EtOAc and 20 ml acetone, dried in vacuum giving 9.3 gram of 1-[2-(2,4-Dimethyl-phenylsulfanyl)-phenyl]-piperazine fumarate (22 mmol) as a white powder in 66% overall yield having a purity of 99.5% by LC-MS.

Example 20

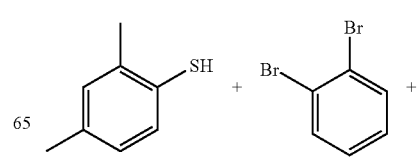

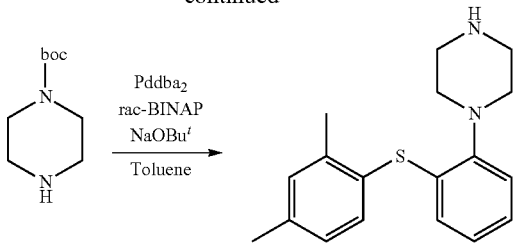

100 g 1,2-dibromobenzene (424 mmol) and 58.6 g 2,4-dimethylthiophenol (424 mmol) are dissolved in 800 ml toluene. The solution is purged with nitrogen before 4.6 g Pddba$_2$ (8 mmol; 2 mol-%) and 13.1 g rac-BINAP (21 mmol; 5 mol-%). The reaction mixture is stirred 5 min during which the colour changes from dark-red to orange. Addition of 61 g NaOBu$^t$ (636 mmol) and 200 ml toluene took place and a heterogeneous mixture was formed instantly. The suspension was heated to 80° C. under nitrogen. After 10 hours the mixture is cooled to 60° C. before adding a slurry of 102.6 g boc-piperazine (551 mmol) and another 61 g NaOBu$^t$ (636 mmol) in 500 ml toluene. The reaction mixture was purged with nitrogen before adding another portion of 4.6 g Pddba$_2$ (8 mmol; 2 mol-%) and 13.1 g rac-BINAP (21 mmol; 5 mol-%). The mixture was heated to reflux this time (110° C.) for another 6 hours or until HPLC shows full conversion. The reaction mixture was cooled on ice for 2 hours before filtering the mixture though a pad of celite. The filter cake is washed with 2×200 ml toluene and the combined filtrates evaporated to 242 g of red oil. The oil was dissolved in 1000 ml MeOH and slowly added 115 ml 48-wt % HBr (aq.) followed by heating to reflux for 2 hours after which full deprotection was detected by HPLC. The mixture was cooled, added 1000 ml EtOAc and the MeOH was removed by evaporation. Addition of 1000 ml Et$_2$O caused a precipitation. Stirring was continued at room temperature for 2 hours before leaving the slurry in the freezer overnight (−18° C.). Filtration and washing twice with 200 ml Et$_2$O produced 172 g brownish solid after drying in vacuum at 40° C. The brownish solid was treated with 1500 ml boiling H$_2$O for 1 hour before cooled to room temperature for another 2 hours. Filtering and drying in vacuum at 40° C. overnight produced 98 g of 4-[2-(2,4-Dimethyl-phenylsulfanyl)-phenyl]-piperazine hydrobromide (61%).

Example 21

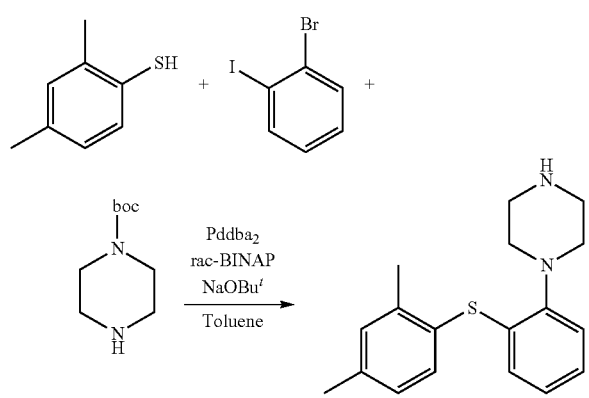

102 g 2-bromo-iodobenzene (362 mmol) and 50 g 2,4-dimethylthiophenol (362 mmol) are dissolved in 1000 ml toluene. To this solution was added 81 g BOC-piperazine (434 mmol) followed by 2.08 g Pddba$_2$ (1 mol %) and 4.51 g rac-BINAP (2 mol %). The mixture was purged with nitrogen for 5 minutes before adding a slurry of 87 g NaOBu$^t$ (905 mmol) in 300 ml toluene. The suspension was heated to 100° C. under nitrogen overnight. A GCMS analysis showed full conversion into the intermediate product (1-(2-Bromo-phenylsulfanyl)-2,4-dimethyl-benzene) and the temperature was increased to reflux (120° C.) for another 24 hours. A HPLC analysis showed full conversion into the intermediate (1-BOC-4-[2-(2,4-Dimethyl-phenylsulfanyl)-phenyl]-piperazine). The reaction mixture was cooled on ice for one hour before filtering the mixture. The filter cake is washed with 2×200 ml toluene and to the combined filtrates was added 80 ml 48-wt % HBr (aq.) followed by heating to reflux for 18 hours after which full deprotection was detected by HPLC. The mixture was cooled on ice for 2 hours and filtrated. The brownish solid was dissolved in 1000 ml boiling H$_2$O for 1 hour together with activated charcoal (25 g), filtered while hot and left to cool. The precipitate was collected by filtration and drying in vacuum at 40° C. overnight produced 49 g of 4-[2-(2,4-Dimethyl-phenylsulfanyl)-phenyl]-piperazine hydrobromide (36%) as a white solid.

Example 22

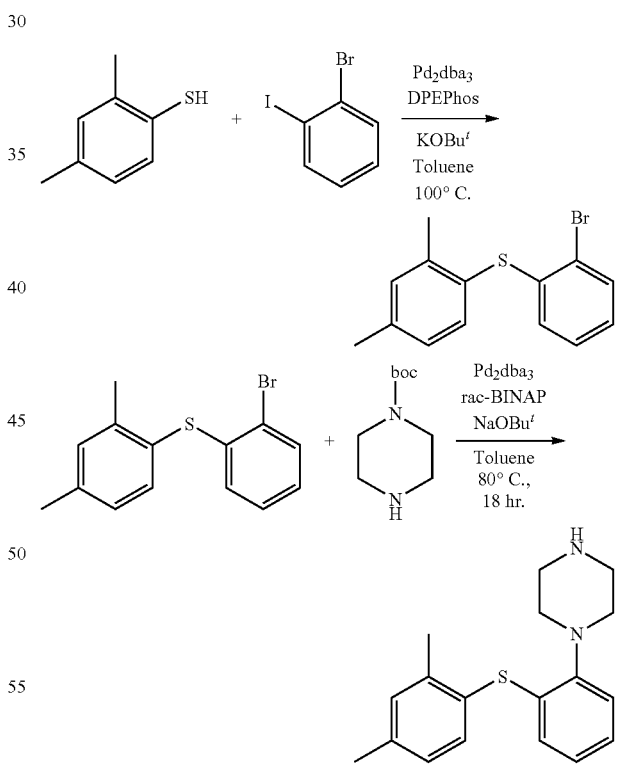

500 ml toluene was placed in a 1 L three-necked round bottle with a mechanical stirrer and added 809 mg Pd$_2$dba$_3$ (0.88 mmol; 0.5 mol-%) and 952 mg DPEPhos (1.77 mmol; 0.5 mol-%). The dark-red solution was purged with nitrogen for 5 minutes before addition of 100 g 2-bromoiodobenzene (353 mmol) and 48.9 g 2,4-dimethylthiophenol (353 mmol) took place. Addition of 43.6 g KOBu$^t$ (389 mmol) caused an exothermic reaction increasing the temperature from 20° C.

to 42° C. simultaneously with the formation of a heterogeneous mixture and the colour changed from dark-red into orange/brownish. The suspension was heated to 100° C. under nitrogen. After only 20 minutes a HPLC showed full conversion into 1-(2-Bromo-phenylsulfanyl)-2,4-dimethyl-benzene. The mixture was cooled to 40° C., added 600 ml 15-wt % NaCl and stirred for 5 minutes. The organic phase was separated and the aqueous phase was washed with 2×100 ml toluene. The combined organic phases were washed with 100 ml 2M HCl(aq.), 100 ml 15-wt % NaCl, dried over $Na_2SO_4$, refluxed for 15 minutes with activated charcoal (10 g), filtered twice and evaporated to 107.3 g orange-red oil (103%) that was found to be 98% pure by HPLC.

A solution of 90 gram of the orange-red oil (307 mmol) in 500 ml dry toluene was added 57 gram boc-piperazine (307 mmol), degassed with nitrogen for 5 minutes, added 1.4 g $Pd_2dba_3$ (1.53 mmol; 0.5 mol-%) and 2.9 g rac-BINAP (4.6 mmol; 1.5 mol-%), degassed for another 2 minutes before adding 35.4 gram $Bu^tONa$ (368 mmol) and heated to 80° C. for 18 hours. HPLC showed full conversion and the reaction mixture was cooled to RT, filtered and the filter cake was washed with 2×100 ml toluene. The combined filtrates was extracted twice with 2×150 ml 15-wt % NaCl, dried over $Na_2SO_4$, added charcoal, refluxed for 30 minutes, filtered twice and evaporated to 140.7 gram of brownish oil (4-[2-(2, 4-Dimethyl-phenylsulfanyl)-phenyl]-BOC-piperazine). The crude oil was dissolved in 300 ml MeOH and 200 ml 6M HCl (aq.) and refluxed for 1 hour after which HPLC showed full deprotection. After cooling to RT the methanol was removed by vacuum on a rotary-evaporator, 200 ml conc. NaOH (pH was measured to 13-14) was added after which the mixture was stirred 15 minutes with 1000 ml EtOAc. The organic phase was collected and extracted with 300 ml 15-wt % brine, dried over $Na_2SO_4$ and added to a solution of 46.3 g fumaric acid (399 mmol) in 300 ml MeOH. The mixture was heated to reflux, cooled to room temperature and then left in the freezer overnight (−18° C.). The precipitate was collected, washed with 100 ml EtOAc and 100 ml acetone, dried in vacuum (50° C.) producing 103.2 g of 1-[2-(2,4-Dimethyl-phenylsulfanyl)-phenyl]-piperazine fumarate (249 mmol) as a white powder in 81% overall yield having a purity of 99% by LC-MS. The fumarate was transfer into the free base (1-[2-(2,4-Dimethyl-phenylsulfanyl)-phenyl]-piperazine) using EtOAc/$H_2O$/conc. NaOH, the organic phase was washed with brine, dried using $Na_2SO_4$, filtered and to the filtrate was added 34 ml 48-wt % HBr (aq.) causing a precipitation of a white solid. The solid was collected, treated with 1000 ml boiling $H_2O$, which upon cooling to room temperature formed a slurry. The final product (1-[2-(2,4-Dimethyl-phenylsulfanyl)-phenyl]-piperazine hydrobromide) was collected by filtration and dried in vacuum (50° C.) producing 83 g of white powder (71% yield overall), CHN (teo.) 56.99; 6.11; 7.39; CHN (found) 57.11; 6.15; 7.35.

Example 23

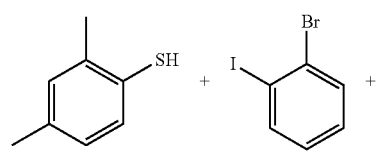

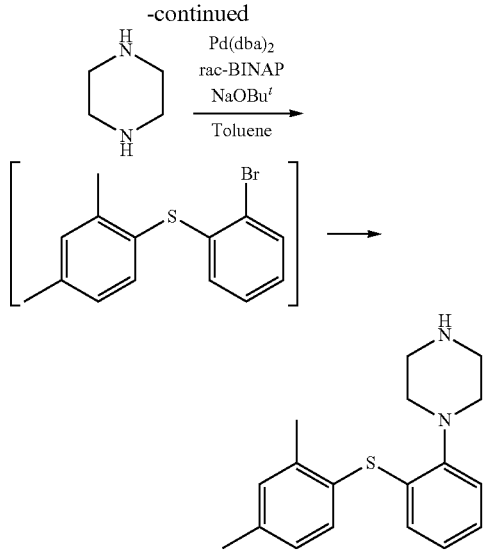

815 g $NaOBu^t$ (8.48 mol), 844 g piperazine (9.8 mol), 6.6 g $Pd(dba)_2$ (11.48 mmol) and 13.6 g rac-BINAP (21.84 mmol) were stirred with 4 L toluene for 50 minutes. 840 g 2-bromo-iodobenzene (2.97 mol) was then added along with 1.5 L Toluene and stirring continued for 30 min. 390.8 g 2,4-dimethylthiophenol (2.83 mol) was finally added with 1.5 L toluene. The suspension was heated to reflux and reflux continued for 5 hours. The reaction mixture was cooled down over night. 2 L water was added and stirred for 1 hour before the mixture was filtrated through filter aid. The filtrate was then washed with 3×1 L brine. The combined water phases were then extracted with 600 ml toluene. The combined toluene phases were then heated to 70° C. followed by addition of 329.2 ml 48-wt % HBr (aq.) and 164.6 ml water. The mixture was cooled to room temperature over night. The final product (1-[2-(2,4-Dimethyl-phenylsulfanyl)-phenyl]-piperazine hydrobromide) was collected by filtration and dried in vacuum (60° C.) producing 895 g (84% yield).

Example 24

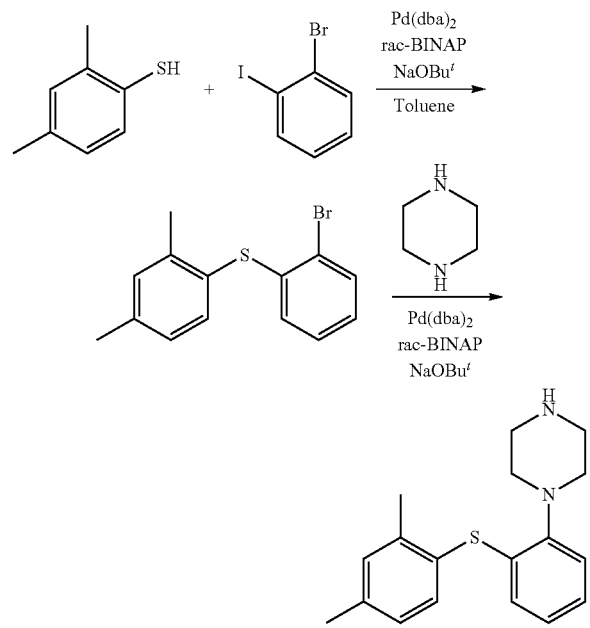

40.76 g NaOBu$^t$ (424.1 mol), 0.33 g Pddba$_2$ (0.57 mmol) and 0.68 g rac-BINAP (1.09 mmol) were stirred with 200 ml toluene. 42 g 2-bromo-iodobenzene (362 mmol) and 19.54 g 2,4-dimethylthiophenol (362 mmol) were added with 50 ml toluene. The suspension was heated to reflux and reflux continued over night. A HPLC analysis showed full conversion into the intermediate product (1-(2-Bromo-phenylsulfanyl)-2,4-dimethyl-benzene). The reaction mixture was cooled to RT and filtered through filter aid. The filtrate was added to a mixture of 40.76 g NaOBu$^t$ (424.1 mmol), 42.2 g piperazine (489.9 mmol), 0.33 g Pddba$_2$ (0.57 mmol) and 0.68 g rac-BINAP (1.09 mmol) and heated to reflux for 2 hours. The reaction mixture was cooled down over night. 100 ml water was added and the water phase separated off. The organic phase was filtered through filter aid and the filtrate was then washed with 3×80 ml brine. The combined water phases were then extracted with 50 ml toluene. The combined toluene phases were then heated to 70° C. and followed by addition of 16.5 ml 48-wt % HBr (aq.) and 8.25 ml water. The mixture was cooled to room temperature over night. The final product (1-[2-(2,4-Dimethyl-phenylsulfanyl)-phenyl]-piperazine hydrobromide) was collected by filtration and dried in vacuum (60° C.) producing 40.18 g of off-white powder (75% yield).

Example 25

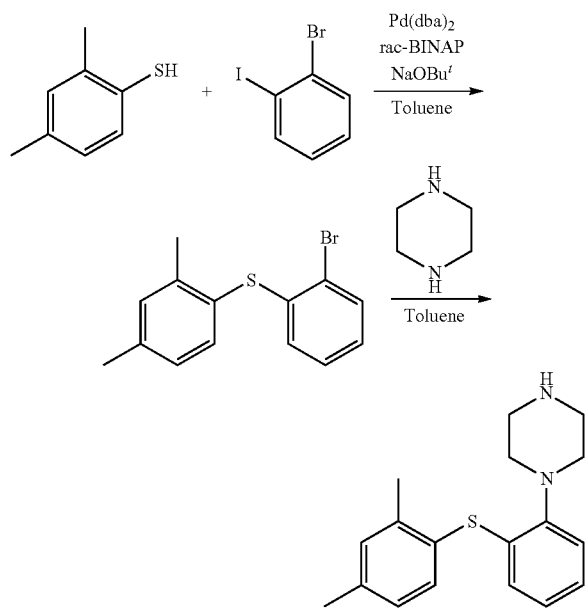

40.76 g NaOBu$^t$ (424.1 mmol), 0.33 g Pddba$_2$ (0.57 mmol) and 0.68 g rac-BINAP (1.09 mmol) were stirred with 200 ml toluene. 42 g 2-bromo-iodobenzene (148.5 mmol) and 19.54 g 2,4-dimethylthiophenol (141.4 mmol) was added with 50 ml toluene. The suspension was heated to reflux and reflux continued over night. A HPLC analysis showed full conversion into the intermediate product (1-(2-Bromo-phenylsulfanyl)-2,4-dimethyl-benzene). Reaction cooled to 50° C. and 42.2 g piperazine (489.9 mmol) was added along with 100 ml toluene. The mixture was heated to reflux for 4 hours. The reaction mixture was cooled to RT over night. 100 ml water was added and the reaction mixture was filtered through filter aid. The filter cake was then washed with 50 ml toluene.

The water phase was separated off and the organic phase was then washed with 3×25 ml brine and 25 ml water. The combined water phases were then extracted with 30 ml toluene. The combined toluene phases was then heated to 70° C. and followed by addition of 16.46 ml 48-wt % HBr (aq.) and 8.23 ml water. The mixture was cooled to room temperature over night. The final product (1-[2-(2,4-Dimethyl-phenylsulfanyl)-phenyl]-piperazine hydrobromide) was collected by filtration and dried in vacuum (60° C.) producing 46.8 g (87% yield).

Example 26

Effects on Extracellular Levels of Acetylcholine in the Brain of Freely Moving Rats Methods
The animals were administered 1-[2-(2,4-dimethylphenylsulfanyl)phenyl]piparazine, HBr salt.
Animals
Male Sprague-Dawley rats, initially weighing 275-300 g, were used. The animals were housed under a 12-hr light/dark cycle under controlled conditions for regular in-door temperature (21±2° C.) and humidity (55±5%) with food and tap water available ad libitum.
Surgery and Microdialysis Experiments
Rats were anaesthetised with hypnorm/dormicum (2 ml/kg) and intracerebral guide cannulas (CMA/12) were stereotaxically implanted into the brain, aiming at positioning the dialysis probe tip in the ventral hippocampus (co-ordinates: 5.6 mm posterior to bregma, lateral −5.0 mm, 7.0 mm ventral to dura) or in the prefrontal cortex (co-ordinates: 3.2 mm anterior to bregma; lateral, 0.8 mm; 4.0 mm ventral to dura). Anchor screws and acrylic cement were used for fixation of the guide cannulas. The body temperature of the animals was monitored by rectal probe and maintained at 37° C. The rats were allowed to recover from surgery for 2 days, housed singly in cages. On the day of the experiment a microdialysis probe (CMA/12, 0.5 mm diameter, 3 mm length) was inserted through the guide cannula.

The probes were connected via a dual channel swivel to a microinjection pump. Perfusion of the microdialysis probe with filtered Ringer solution (145 mm NaCl, 3 mM KCl, 1 mM MgCl$_2$, 1.2 mM CaCl$_2$ containing 0.5 µM neostigmine) was begun shortly before insertion of the probe into the brain and continued for the duration of the experiment at a constant flow rate of 1 µl/min. After 180 min of stabilisation, the experiments were initiated. Dialysates were collected every 20 min. After the experiments the animals were sacrificed, their brains removed, frozen and sliced for probe placement verification.

The compound dissolved in 10% HPbetaCD and injected subcutaneously (2.5-10 mg/kg). Doses are expressed as mg salt/kg body weight. The compound was administered in a volume of 2.5 ml/kg.
Analysis of Dialysate Acetylcholine
Concentration of acetylcholine (ACh) in the dialysates was analysed by means of HPLC with electrochemical detection using a mobile phase consisting of 100 mM disodium hydrogenphosphate, 2.0 mM octane sulfonic acid, 0.5 mM tetramethyl-ammonium chloride and 0.005% MB (ESA), pH 8.0. A pre-column enzyme reactor (ESA) containing immobilised choline oxidase eliminated choline from the injected sample (10 µl) prior to separation of ACh on the analytical column (ESA ACH-250); flow rate 0.35 ml/min, temperature: 35° C. After the analytical column the sample passed through a post-column solid phase reactor (ESA) containing immobilised acetylcholineesterase and choline oxidase. The latter reactor converted ACh to choline and subsequently choline to betaine and $H_2O_2$. The latter was detected electrochemical by using a platinum electrode (Analytical cell: ESA, model 5040).

Data Presentation

In single injection experiments the mean value of 3 consecutive ACh samples immediately preceding compound administration served as the basal level for each experiment and data were converted to percentage of basal (mean basal pre-injection values normalized to 100%).

Results

The compound significantly increased extra-cellular levels of ACh in the rat prefrontal cortex and the ventral hippocampus—see FIGS. 19a and 19b.

Example 27

Contextual Fear Conditioning in Rats

The compound administered in the present experiment was 1-[2-(2,4-dimethylphenylsulfanyl)phenyl]piperazine HBr salt.

We have studied the effect of the compound on acquisition, consolidation and recall of contextual fear conditioning in rats. In the fear conditioning paradigm animals learn to associate a neutral environment (context, the training chamber, CS) with an aversive experience (an electrical foot-shock, US). During re-exposure to the training chamber, animals express a freezing behaviour, which is taken as a direct measure of the fear-related memory [*Pavlov J. Biol. Sci.*, 15, 177-182, 1980]. The neuroanatomy of contextual fear conditioning has been thoroughly investigated and several studies have demonstrated that the hippocampus and amygdala are necessary for the formation of this memory [*Hippocampus*, 11, 8-17, 2001; *J. Neurosci.*, 19, 1106-1114, 1999; *Behav. Neurosci.*, 106, 274-285, 1992].

Animals and Drugs

Adult male Sprague-Dawley rats (weighing 250-300 g at time of training) from Charles River Laboratories, housed two per cage under a 12 h light/dark cycle, were used. Food and water were available ad libitum. Rats were used 1 week after arrival. The compound was dissolved in 10% HPbetaCD and injected subcutaneously. The drug was administered in a volume of 2.5 ml/kg.

Apparatus

Training and testing were conducted in a soundproof chamber (30×20×40 cm) housed in an isolated room and connected to a ventilation system. Illumination was provided by a white light (60 Watt). The floor of the chamber consisted of a metal grid attached to an electric shock generator. Prior to training and testing, the chamber was cleaned with a 70% ethanol solution. A video camera allowed for behavioral observations and recording of the training session for off-line analysis.

Acquisition and Retention Test

During the acquisition animals were allowed to freely explore the novel environment for a 1 min habituation period, which co-terminated with one inescapable foot-shock (unconditioned stimulus, US) through the electrifiable grid floor. The foot shock had a duration of 2 s and an intensity of 0.75 mA. Animals remained in the conditioning chamber for another 60 s after the US. Freezing behaviour was scored during the first 58 s (pre-shock acquisition; experimenter blinded to groups) to determine baseline-freezing responses to the context. At the end of the acquisition animals were gently removed and placed into their home cages. After 24 h the same animals were reintroduced into the training context (fear conditioning chamber) and a 2 min retention test was performed. During this period no foot shocks were applied. Freezing behaviour was scored during the whole test period with the experimenter blinded to groups and presented as percent of total test period.

Results and Discussion

Effect of the Compound on Contextual Fear Cognition in Rats

The effect of the compound on contextual fear conditioning in rats was studied (i) on acquisition (drug applied before acquisition, FIG. 20), (ii) on memory recall (drug applied before test, FIG. 21) and (iii) on consolidation (drug applied immediately after the acquisition, FIG. 22). In the first set of experiments, the compound (1, 5 and 10 mg/kg) was administered 1 h prior to the acquisition session. FIG. 20 depicts the acquisition of freezing behavior during training (58 s prior to the food shock) and the retention test 24 after. The following findings were observed:

The compound does not affect baseline freezing behaviour before the presentation of the foot shock at any dose tested.

The compound at 5 mg/kg has a tendency to increase the time spent freezing during the retention test, 24 h after the acquisition (39.24±13.76%, n=6, versus 24.30±4.40%, n=16, in the vehicle-treated animals).

The compound at 10 mg/kg significantly increases the time spent freezing during the retention test, 24 h after the acquisition (52.15±5.68%, n=10, versus 24.30±4.40%, n=16, in the vehicle-treated animals, p<0.01).

The fear conditioning model, as described in FIG. 20, is a standard procedure described in the literature for the investigation of learning and memory. In order to further elucidate the acute effects of this drug on memory recall, the compound (5, 10 and 20 mg/kg) was applied 1 h prior to the retention test. It was observed that the compound inhibits the expression of freezing behaviour at 5 mg/kg during the memory test (12.86±3.57%, n=9, versus 33.61±4.29%, n=13, in the vehicle-treated animals, p<0.05) (FIG. 21).

As described above, the compound by itself does not affect baseline freezing behaviour before the onset of US (FIG. 20), thus the most plausible hypothesis is that the observed effect in FIG. 21 is due to an anxiolytic effect. The conditioned memory is assessed via freezing behaviour, a response that is reduced by compounds with potential anxiolytic effects. This experiment demonstrates that the compound given acutely before memory recall has anxiolytic efficacy, it is therefore unlikely that increased freezing shown in FIG. 20 is due to an anxiogenic effect of the compound.

In order to strengthen that the compound is not anxiogenic but bears pro-cognitive potential, the compound was administered at 5, 10 and 20 mg/kg after the acquisition session. Consequently, in this set of experiments, the compound was onboard neither during the acquisition nor throughout the retention test. Here, it was observed that the compound at 5 mg/kg significantly enhances the time spent freezing during the retention test, 24 h after the acquisition session (45.58±4.50%, n=8, versus 25.26±3.57%, n=19, in the vehicle-treated animals, p<0.05). The percentage of time spent freezing during the context re-exposure has been described as a measure of a fear-related memory [*Pavlov J. Biol. Sci*, 15, 177-182, 1980], which is enhanced in compound-treated rats when compared to vehicle-treated animals (FIGS. 20 and 21). Taken together, the data show that the compound enhances contextual memory.

The invention claimed is:

1. A method of treating a disease selected from the group consisting of affective disorders, depression, major depressive disorder, anxiety, general anxiety disorder, social anxiety disorder, obsessive compulsive disorder, panic disorder, and panic attacks, the method comprising administering a therapeutically effective amount of a hydrobromide salt of Compound I to a patient in need thereof, wherein Compound I is 1-[2-(2,4-dimethylphenylsulfanyl)-phenyl]piperazine, the hydrobromide salt of Compound I is a crystalline compound characterized by XRPD reflections at 6.89, 9.73, 13.78 and 14.64+/−0.10° 2θ, and the method alleviates a symptom or complication of the disease or delays the progression of the disease.

2. The method of claim 1, wherein the hydrobromide salt is characterized by an XRPD as shown in FIG. 3.

3. The method of claim 1, wherein the hydrobromide salt has a particle size distribution corresponding to:

D98%: 650-680 µm; D50%: 230-250 µm; and D5%: 40-60 µm;

D98%: 370-390 µm; d50%: 100-120 µm; and D5%: 5-15 µm;

D98%: 100-125 µm; D50%: 15-25 µm; and D5%: 1-3 µm; or

D98%: 50-70 µm; D50%: 3-7 µm; and D5%: 0.5-2 µm.

4. The method of claim 1, wherein the disease is major depressive disorder.

5. The method of claim 1, wherein the disease is depression or major depressive disorder.

* * * * *